United States Patent [19]
Bernardon et al.

[11] Patent Number: 5,574,036
[45] Date of Patent: Nov. 12, 1996

[54] ADAMANTYL-SUBSTITUTED POLYCYCLIC ACETYLENE COMPOUNDS AND PHARMACEUTICAL/COSMETIC COMPOSITIONS COMPRISED THEREOF

[75] Inventors: Jean-Michel Bernardon, Le Rouret; Bruno Charpenter, Biot, both of France

[73] Assignee: Centre International de Recherches Dermatologiques Galderma, Valbonne, France

[21] Appl. No.: 429,045

[22] Filed: Apr. 26, 1995

[30] Foreign Application Priority Data

Apr. 26, 1994 [FR] France .................. 94-05018

[51] Int. Cl.$^6$ .............. A61K 31/19; A61K 31/535; C07C 63/64; C07D 295/112
[52] U.S. Cl. .............. 514/239.2; 424/69; 514/569; 514/828; 514/844; 514/845; 514/846; 514/847; 514/848; 514/859; 514/861; 514/863; 514/871; 514/912; 544/154; 546/322; 549/79; 549/454; 560/255; 562/451; 562/466; 562/467; 564/172; 568/439; 568/609; 585/352
[58] Field of Search .................. 544/154; 562/466; 514/239.2

[56] References Cited

FOREIGN PATENT DOCUMENTS 0176034 4/1986 European Pat. Off. .

OTHER PUBLICATIONS

Chemical Abstracts, vol. 87, No. 3, Jul. 18, 1977, Columbus, Ohio; abstract No. 22693b, Musantaeva, SH. et al, "Synthesis of P–Acetylenybenzoic Acid", p. 599, col. 2; & Deposited doc., 1974, pp. 297–75, Viniti.

*Primary Examiner*—Robert W. Ramsuer
*Attorney, Agent, or Firm*—Burns, Doane, Swecker & Mathis, L.L.P.

[57] ABSTRACT

Novel pharmaceutically/cosmetically-active adamantyl-substituted polycyclic acetylene compounds have the structural formula (I):

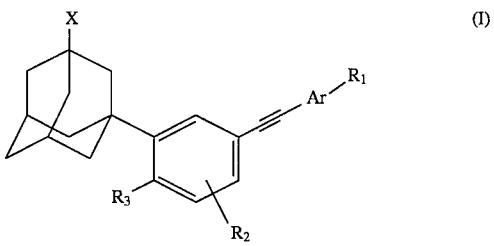

wherein Ar is a radical having one of the formulae (a)–(f):

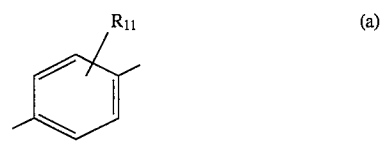

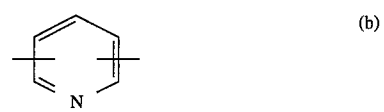

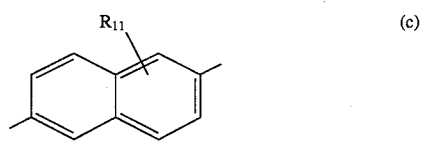

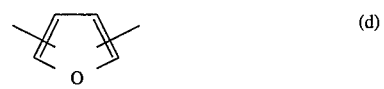

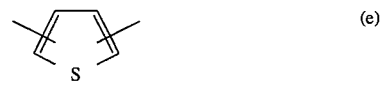

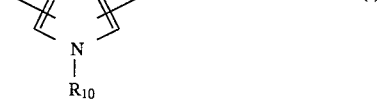

and are useful for the treatment of a wide variety of disease states, whether human or veterinary, for example dermatological, rheumatic, respiratory, cardiovascular, bone and ophthalmological disorders, as well as for the treatment of mammalian skin and hair conditions/disorders.

42 Claims, 2 Drawing Sheets

ADAMANTYL-SUBSTITUTED POLYCYCLIC ACETYLENE COMPOUNDS AND PHARMACEUTICAL/COSMETIC COMPOSITIONS COMPRISED THEREOF

CROSS-REFERENCE TO COMPANION APPLICATIONS

Copending applications Ser. No. 08/429,096 [Attorney Docket No. 016800-023] and Ser. No. 08/429,492 [Attorney Docket No. 016800-024], both filed concurrently herewith and assigned to the assignee hereof. Cf. copending applications Ser. No. 08/356,913 [Attorney Docket No. 016800-006], Ser. No. 08/357,024 [Attorney Docket No. 016800-007] and Ser. No. 08/356,680 [Attorney Docket No. 016800-008], each filed Dec. 15, 1994 and each also assigned to the assignee hereof.

BACKGROUND OF THE INVENTION

TECHNICAL FIELD OF THE INVENTION

The present invention relates to novel adamantyl-substituted polycyclic acetylene compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention display marked activity in the fields of cell differentiation and proliferation and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degenerative diseases of the connective tissue, for controlling aging of the skin, whether photoinduced or chronological, and for treating healing disorders. Moreover, they are also useful for ophthalmological applications, especially for the treatment of corneopathies.

The compounds of this invention are also useful for the treatment of osteoporosis or for the treatment of viral diseases, as well as for the treatment of any condition related to a hypervitaminosis A. Generally, they are useful for the treatment of any disease state which is associated with a modification in the expression of receptors belonging to the superfamily of receptors for steroidal and thyroid hormones.

Too, the compounds according to this invention can also be formulated into cosmetic compositions for body and hair care/hygiene.

Briefly, the polycyclic acetylene compounds according to this invention have the following structural formula (I):

(I)

in which X is a hydrogen atom or a halogen atom; $R_1$ is a hydrogen atom, a —$CH_3$ radical, a —$CH_2$—O—$R_4$ radical, a —$CH_2$—O—CO—$R_5$ radical, an —O—$R_6$ radical, an —O—$(CH_2)_m$—$(CO)_n$—$R_7$ radical, a —$(CH_2)_p$—CO—$R_8$ radical, a —$(CH_2)_p$—CO—O—$R_9$ radical or an —$S(O)_p$—$R_{10}$ radical, wherein m, n and p and the radicals $R_4$ to $R_{10}$ are as defined below; Ar is a radical selected from among those of the following formulae (a)–(f):

(a)

(b)

(c)

(d)

(e)

(f)

wherein $R_{10}$ and $R_{11}$ are as defined below; $R_2$ is a hydrogen atom or a halogen atom, a linear or branched alkyl radical having from 1 to 20 carbon atoms, an —O—$CH_2$—O—$CH_2$—$CH_2$—O—$CH_3$ radical or an —O—$R_{13}$ radical, wherein $R_{13}$ is as defined below; $R_3$ is an —O—$CH_2$—O—$CH_2$—$CH_2$—O—$CH_3$ radical, a —$(Y)_n$—$(CH_2)_q$—$R_{14}$ radical, a —$(CH_2)_m$—Y—$(CH_2)_q$—$R_{14}$ radical or a —CH=CH—$(CH_2)_t$—$R_{14}$, radical, wherein m, n, q and t and the Y and $R_{14}$ radicals are as defined below; m is an integer equal to 1, 2 or 3, n is an integer equal to 0 or 1, p is an integer equal to 0, 1, 2 or 3, q is an integer ranging from 0 to 12, inclusive, and t is an integer ranging from 0 to 10, inclusive; $R_4$ is a hydrogen atom or a lower alkyl radical; $R_5$ is a lower alkyl radical; $R_6$ is a hydrogen atom or a lower alkyl radical; $R_7$ is a lower alkyl radical or a heterocycle; $R_8$ is a hydrogen atom, a lower alkyl radical, or a radical:

in which R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a nitrogen-containing heterocycle; $R_9$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_{10}$ is a hydrogen atom or a lower alkyl radical; $R_{11}$ is a hydrogen atom, a halogen atom, a lower alkyl radical, a hydroxyl radical, or an —O—$R_{12}$ or —O—CO$R_{12}$ radical, wherein $R_{12}$ is as defined below; $R_{12}$ is a lower alkyl radical; $R_{13}$ is a hydrogen atom or a linear or branched alkyl radical having from 1 to 20 carbon atoms; $R_{14}$ is a hydrogen atom, a lower alkyl radical, an alkenyl radical, an alkynyl radical, a $C_3$-$C_6$ cycloaliphatic radical, a mono- or polyhydroxyalkyl radical, said hydroxyls optionally being protected as methoxy, acetoxy or acetonide groups, an aryl or aralkyl radical, a —CO—$R_8$ radical, a —COO$R_9$ radical, an —S(O)$_p$—$R_{10}$ radical, a radical:

or, but only in the event that n is equal to 0 and $R_3$ is —(Y)$_n$—(CH$_2$)—$R_{14}$, a hydroxyl radical, an —O—$R_{12}$ radical or an —O—CO$R_{12}$ radical; and Y is an oxygen or sulfur atom or an —S(O)$_p$ radical.

This invention also features the salts of the compounds of formula (I) in the event that the $R_1$ radical or $R_{14}$ radical represents a carboxylic acid functional group or a sulfonic acid functional group, or, alternatively, when the $R_{14}$ radical represents an amine functional group, as well as the chiral (optical) and geometric isomers thereof. When the compounds according to the invention exist in the form of salts, they are preferably salts of an alkali metal or alkaline earth metal, or, alternatively, of zinc or of an organic amine.

DETAILED DESCRIPTION OF BEST MODE AND PREFERRED EMBODIMENTS OF THE INVENTION

More particularly according to the present invention, by "lower alkyl radical" is intended an alkyl radical having from 1 to 6 carbon atoms and preferably the methyl, ethyl, isopropyl, butyl, tert-butyl and hexyl radicals.

By "linear or branched alkyl radical having from 1 to 20 carbon atoms" is preferably intended methyl, ethyl, propyl, 2-ethylhexyl, octyl, dodecyl, hexadecyl and octadecyl radicals.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having from 3 to 6 carbon atoms and from 2 to 5 hydroxyl groups, such as the 2,3-dihydroxypropyl, 2,3,4-trihydroxybutyl or 2,3,4,5-tetrahydroxypentyl radicals, or the pentaerythritol residue.

By "aryl radical" is preferably intended a phenyl radical optionally substituted by at least one halogen atom, or a hydroxyl or nitro functional group.

By "aralkyl radical" is preferably intended a benzyl or phenethyl radical optionally substituted by at least one halogen atom, or a hydroxyl or nitro functional group.

By "alkenyl radical" is intended a radical preferably having from 2 to 5 carbon atoms and one or more sites of ethylenic unsaturation, such as, more particularly, the allyl radical.

By "alkynyl radical" is preferably intended a radical having from 2 to 6 carbon atoms and at least one site of acetylenic unsaturation, such as the propargyl radical.

By "sugar residue" is intended a residue derived especially from glucose, galactose or mannose, or alternatively from glucuronic acid.

By "amino acid residue" is especially intended a residue derived from lysine, glycine or aspartic acid, and by "peptide residue" is more particularly intended a dipeptide or tripeptide residue prepared via the combination of amino acids.

Lastly, by "heterocycle" is preferably intended a piperidino, morpholino, pyrrolidino or piperazino radical, optionally substituted in the 4-position by a $C_1$-$C_6$ alkyl or mono- or polyhydroxyalkyl radical, as defined above.

When the X, $R_2$ and $R_{11}$ radicals are halogen atoms, they are preferably fluorine, chlorine or bromine atoms.

Among the compounds of formula (I) according to the present invention, particularly representative are the following:

4-[3-(1-adamantyl)-4-methoxyphenylethynyl]benzoic acid;

4-[3-(1-Adamantyl)-4-methoxyethoxymethoxyphenylethynyl]benzoic acid;

4-[3-(1-Adamantyl)-4-hydroxyphenylethynyl]benzoic acid;

5-[3-(1-Adamantyl)-4-methoxyphenylethynyl]-2-thiophenecarboxylic acid;

5-[3-(1-Adamantyl)-4-hydroxyphenylethynyl]-2-thiophenecarboxylic acid;

2-[3-(1-Adamantyl)-4-methoxyphenylethynyl]-4-thiophenecarboxylic acid;

6-[3-(1-Adamantyl)-4-methoxyphenylethynyl]-2-naphthoic acid;

4-[3-(1-Adamantyl)-4-nonyloxyphenylethynyl]benzoic acid;

4-[3-(1-Adamantyl)-4-hexyloxyphenylethynyl]benzoic acid;

4-[3-(1-Adamantyl)-4-dodecyloxyphenylethynyl]benzoic acid;

4-[3-(1-Adamantyl)-4-cyclopropylmethoxyphenylethynyl]benzoic acid;

4-[2-Hexyloxy-5-(1-adamantyl)-4-hexyloxyphenylethynyl]benzoic acid;

4-[3-(1-Adamantyl)-4-heptyloxyphenylethynyl]benzoic acid;

6-[3-(1-Adamantyl)-4-methoxyethoxymethoxyphenylethynyl]nicotinic acid;

4-[2-Methoxy-5-(1-adamantyl)-4-methoxyphenylethynyl]benzoic acid;

4-[2-Methoxyethoxymethoxy-5-(1-adamantyl)-4-methoxyethoxymethoxyphenylethynyl]benzoic acid;

4-[2-Methoxy-5-(1-adamantyl)-4-methoxyethoxymethoxyphenylethynyl]benzoic acid;

4-[3-(1-Adamantyl)-4-benzyloxyphenylethynyl]benzoic acid;

4-[3-(1-Adamantyl)-4-methoxyethoxymethoxyphenylethynyl]benzaldehyde;

4-[3-(1-Adamantyl)-4-methoxyethoxymethoxyphenylethynyl]benzenemethanol;

4-[3-(1-Adamantyl)-4-methoxyethoxymethoxyphenyl-
ethynyl]benzyl acetate;

4-[3-(1-Adamantyl)-4-methoxyethoxymethoxyphenyl-
ethynyl]phenyl acetate;

4-[3-(1-Adamantyl)-4-methoxyethoxymethoxyphenyl-
ethynyl]phenol;

4-[3-(1-Adamantyl)-4-methoxyethoxymethoxyphenyl-
ethynyl]phenoxyethylmorpholine;

4-[3-(1-Adamantyl)-4-methoxyethoxymethoxyphenyl-
ethynyl]benzamide;

N-Ethyl-4-[3-(1-adamantyl)-4-methoxyethoxymethox-
yphenylethynyl]benzamide;

4-[3-(1-Adamantyl)-4-methoxyethoxymethoxyphenyl-
ethynyl]benzoic acid morpholide;

2-Hydroxy-4-[3-(1-adamantyl)-4-methoxy-
ethoxymethoxyphenylethynyl]benzoic acid;

4-[3-(1-Adamantyl)-4-(6-hydroxyhexyloxy)phenylethy-
nyl]benzoic acid;

4-[3-(1-Adamantyl)-4-(6-methoxyhexyloxy)phenylethy-
nyl]benzoic acid;

4-[[3-(1-Adamantyl)-4-[2-(4-morpholino)ethoxy]phenyl-
ethynyl]]benzoic acid;

4-[3-(1-Adamantyl)-4-(3-carbamoylpropyloxy)phenyl-
ethynyl]benzoic acid;

4-[3-(1-Adamantyl)-4-(5-carbamoylpentyloxy)phenyl-
ethynyl]benzoic acid;

4-[3-(1-Adamantyl)-4-(3-hydroxypropyloxy) phenyl-
ethynyl]benzoic acid;

4-[3-(1-Adamantyl)-4-(3-hydroxy-2-methylpropylox-
y)phenylethynyl]benzoic acid;

4-[3-(1-Adamantyl)-4-[(2,2-dimethyl1,3-dioxolan-4-
methoxy)phenylethynyl]benzoic acid;

4-[3-(1-Adamantyl)-4-(2,3-dihydroxypropyloxy)phenyl-
ethynyl]benzoic acid;

4-[3-(1-Adamantyl)-4-methoxyethoxyethylphenylethy-
nyl]benzoic acid;

4-[3-(1-Adamantyl)-4-methoxymethoxypropylphenyl-
ethynyl]benzoic acid;

4-[3-(1-Adamantyl)-4-methoxyethoxypropylphenyl-
ethynyl]benzoic acid;

4-[3-(1-Adamantyl)-4-acetoxybutoxyphenylethynyl]ben-
zoic acid;

4-[3-(1-Adamantyl)-4-acetoxypropyloxyphenylethynyl]
benzoic acid.

According to the present invention, the more particularly preferred compounds of formula (I) are those in which at least one, and preferably all, of the conditions given below are satisfied:

$R_1$ is a —$(CH_2)_p$—CO—$R_8$ radical;

$R_3$ is an —O—$CH_2$—O—$CH_2$—$CH_2$—O—$CH_3$ or —$(Y)_n$—$(CH_2)_q$—$R_{14}$ radical;

Ar is a radical selected from among those of formulae (a) and (e); and $R_2$ is a linear or branched alkyl radical having from 1 to 20 carbon atoms or, alternatively, an —O—$R_{13}$ radical.

Figure 1:
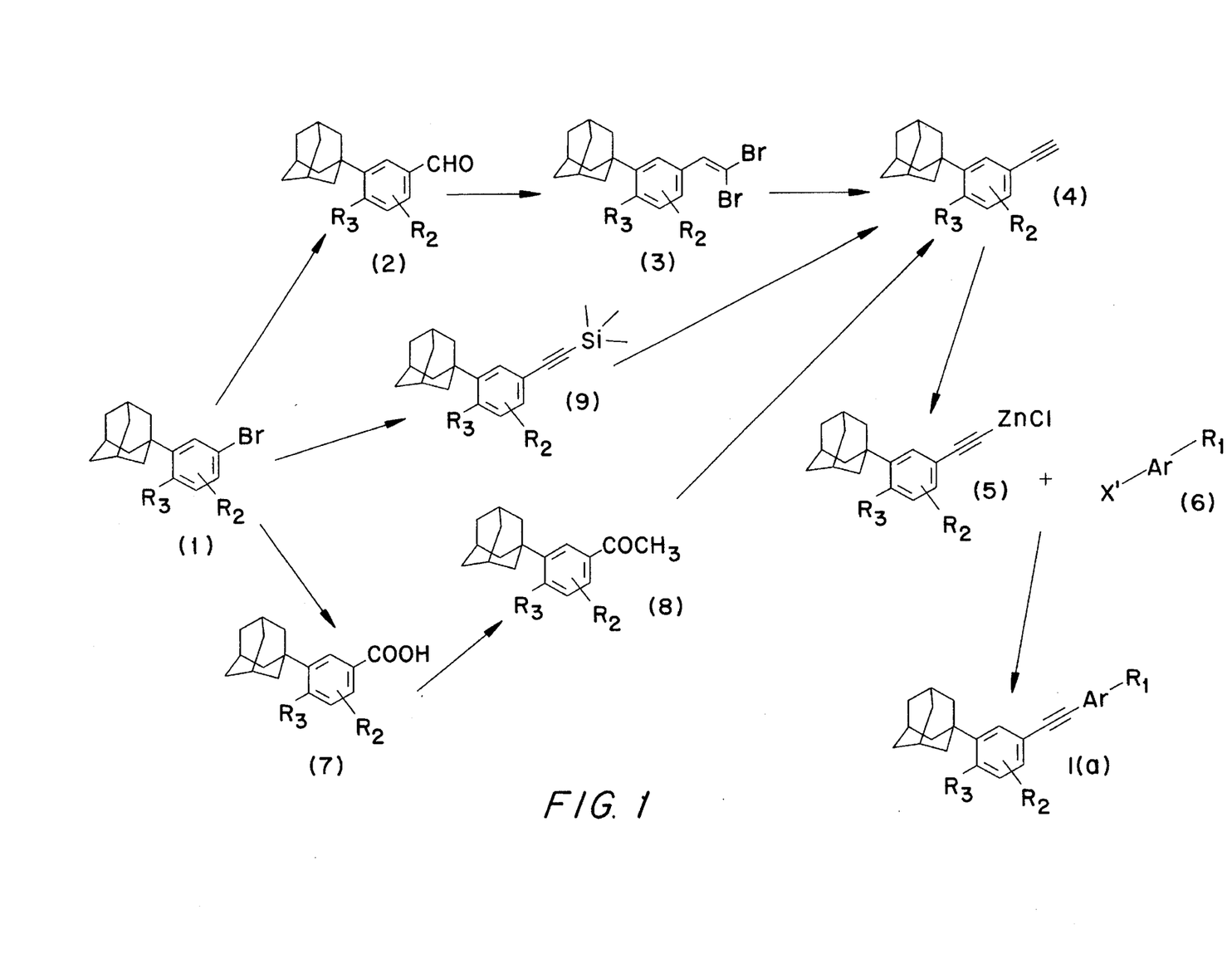
FIGS. 1 and 2 set forth reaction schemes/mechanisms illustrating representative syntheses for the preparation of the polycyclic acetylene compounds according to the present invention.
Figure 2:
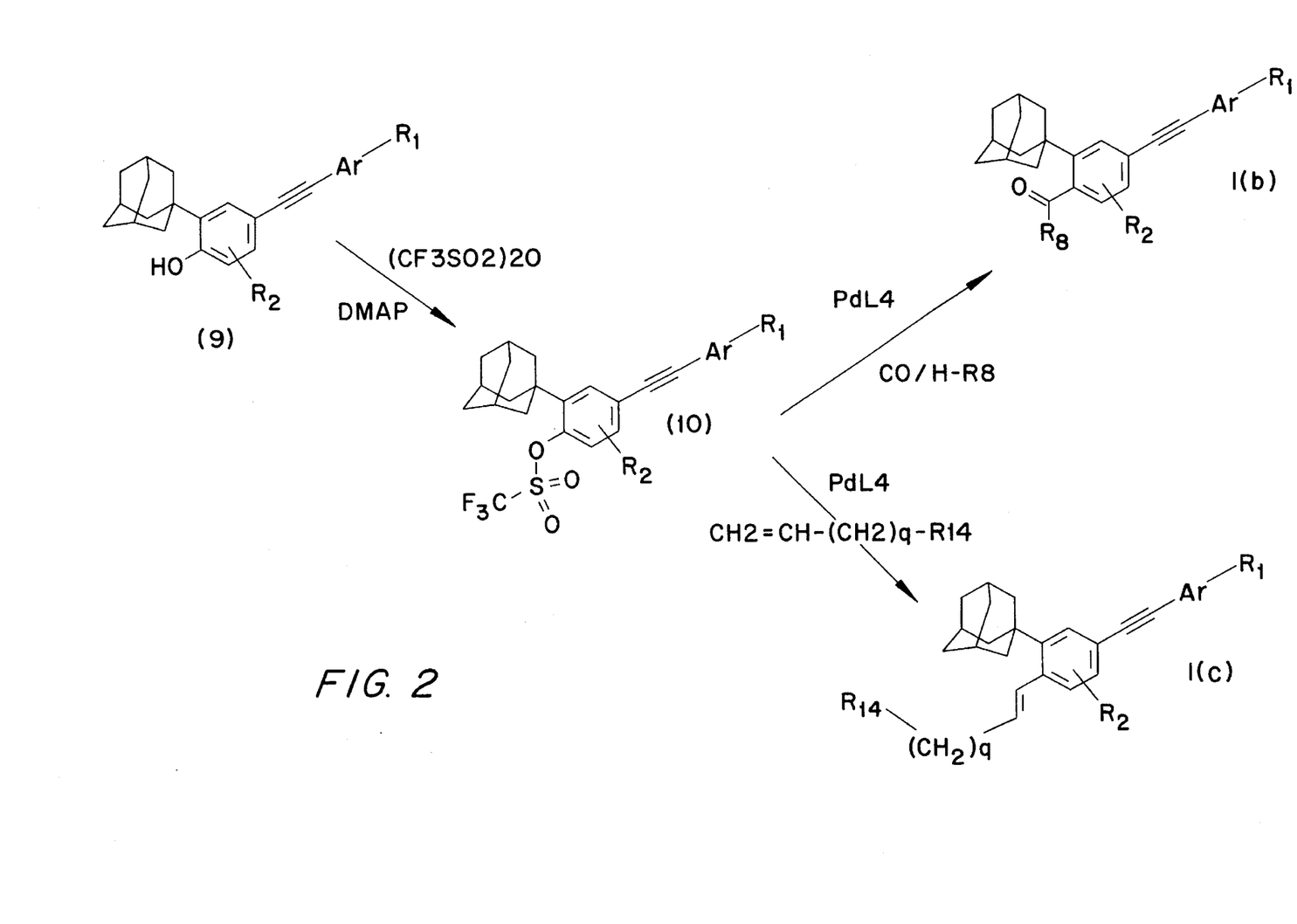

The present invention also features the processes for the preparation of the compounds of formula (I), in particular via the reaction schemes illustrated in FIGS. 1 and 2.

Thus, the compounds of formula I(a) can be prepared (FIG. 1) from the acetylene derivative (4) by conversion into a lithium and then zinc derivative (5). Such derivative is then coupled with the halogenated derivative (6) (preferably the iodinated or brominated derivative) in the presence of a palladium catalyst (preferably tetrakis(triphenylphosphine-)palladium(0)) in a solvent such as THF.

The acetylene derivative (4) can, in its turn, be obtained from the brominated derivative (1) via three different techniques:

(i) either by conversion into an aldehyde compound (2) by reacting the magnesium or lithium derivative with dimethylformamide. The aldehyde (2) then reacts with carbon tetrabromide and triphenylphosphine to give a 2',2'-dibromostyrene derivative (3) which is then converted to the acetylene derivative (4) by means of a non-nucleophilic base such as n-butyllithium in an aprotic solvent such as tetrahydrofuran;

(ii) or by conversion to the acid derivative (7) by reacting the magnesium or lithium derivative with $CO_2$. The acid (7), in the presence of a large excess of methyllithium, is then converted to a ketone derivative (8) which, by a sequence of reactions (treatment with a base such as lithium diisopropylamide and then with a dialkyl chlorophosphate and again with lithium diisopropylamide) is ultimately converted into the acetylene derivative (4);

(iii) or by conversion into the trimethylsilylacetylene derivative (9) by reaction with trimethylsilylacetylene in a solvent such as triethylamine in the presence of palladium acetate and triphenylphosphine and then desilylation in the presence either of potassium carbonate or of tetrabutylammonium fluoride.

In the aforesaid formulae and reactions $R_1$, $R_2$ and $R_3$ are as defined above in respect of the compounds of formula (I) or are derivatives thereof which are suitably protected as to be compatible with the coupling conditions. In particular, when they represent the hydroxyl radical, the latter is preferably protected in the tert-butyldimethylsilyloxy or methoxyethoxymethoxy form. Deprotection is then carried out either in the presence of tetrabutylammonium fluoride or trimethylsilyl iodide or in acidic medium (for example HCl).

When $R_3$ is a —$(CH_2)_q$—CO—$R_8$ radical or a —CH=CH—$(CH_2)_r$—$R_{14}$ radical, the compounds are preferably prepared from the phenol derivative (9) according to the reaction scheme illustrated in FIG. 2, namely, conversion of the phenol derivative (9) into the triflate (10) and then nucleophilic substitution in the presence of a palladium catalyst (for example tetrakis(triphenylphosphine-)palladium(0)) according to the general conditions described in S. Cacchi et al, *Tetrahedron Letters*, 27, 3931–4 (1986) or in W. J. Scott et al, *J. Org. Chem.*, 50, 2302–8 (1985).

The present invention also features therapeutic/pharmaceutical applications of the compounds of formula (I).

Depending on the nature of the radicals used, these compounds exhibit either an agonist activity in the test for differentiation of embryonic teratocarcinoma cells (F9) in mice (*Cancer Research*, 43, p. 5268 (1983)) and/or in the test for inhibition of ornithine decarboxylase after induction by TPA in mice (*Cancer Research*, 38, p. 793–801 (1978)) or, in contrast, an antagonist activity with respect to the expression of one or more biological markers in the test for differentiation of embryonic teratocarcinoma cells (F9) in mice (*Skin Pharmacol.*, 3, pp. 256–267 (1990)) and/or for the in vitro differentiation of human keratinocytes (*Anal. Biochem.*, 192, pp. 232–236 (1991)).

The compounds according to the invention are particularly well suited in the following fields of therapy:

(1) for treating dermatological conditions associated with a keratinization disorder related to differentiation and proliferation, in particular for treating acne vulgaris, comedonic or polymorphic acne, acne rosacea, nodulocystic acne, acne conglobata, senile acne and secondary acnes such as solar, drug or occupational acne, (2) for treating other types of keratinization disorders, in particular ichthyoses, ichthyosiform conditions, Darier's disease, palmoplantar keratoderma, leucoplakia and leucoplakiform conditions or cutaneous or mucosal (oral) lichen, (3) for treating other dermatological conditions associated with a keratinization disorder manifesting an inflammatory and/or immunoallergic component and, in particular, all forms of psoriasis, whether cutaneous, mucosal or ungual, and even psoriatic rheumatism, or alternatively cutaneous or skin atopy, such as eczema, or respiratory atopy or alternatively gingival hypertrophy; the compounds can also be used in certain inflammatory conditions not exhibiting keratinization disorder, (4) for treating all dermal or epidermal proliferations, whether benign or malignant, whether or not of viral origin, such as common warts, flat warts and epidermodysplasia verruciformis, florid oral papillomatoses and the proliferations which can be induced by ultraviolet radiation, in particular in the case of basal cell and prickle cell epithelioma, (5) for treating other dermatological disorders, such as bullous dermatoses and collagen diseases, (6) for treating certain opthalmological disorders, in particular corneopathies, (7) for repairing or controlling aging of the skin, whether photoinduced or chronologic, or for reducing actinic keratoses and pigmentations, or any pathology associated with chronologic or actinic aging, (8) for preventing or treating the stigmata of epidermal and/or dermal atrophy induced by local or systemic corticosteroids, or any other form of cutaneous atrophy, (9) for preventing or treating disorders of healing, or for preventing or for repairing stretch marks, (10) for controlling disorders of the sebaceous function, such as hyperseborrhoea of acne or simple seborrhoea, (11) for the treatment or prevention of cancerous or precancerous conditions, (12) for the treatment of inflammatory conditions such as arthritis, (13) for the treatment of any condition of viral origin at the cutaneous or general level, (14) for the prevention or treatment of alopecia, (15) for the treatment of dermatological or general conditions including an immunological component, (16) for the treatment of ailments of the cardiovascular system, such as arteriosclerosis, (17) for the treatment or prevention of osteoporosis.

For the aforesaid therapeutic or pharmaceutical applications, the compounds according to the invention can advantageously be used in combination with other compounds displaying a retinoid-type activity, with vitamins D or derivatives thereof, with corticosteroids, with compounds which control free radicals, α-hydroxy or α-keto acids or derivatives thereof, or alternatively with ion channel blockers. By "vitamins D or derivatives thereof" are intended, for example, derivatives of vitamin $D_2$ or $D_3$ and in particular 1,25-dihydroxyvitamin $D_3$. By "compounds which control free radicals" are intended, for example, α-tocopherol, superoxide dismutase, ubiquinol or certain metal chelating agents. By "α-hydroxy or α-keto acids or derivatives thereof" are intended, for example, lactic, malic, citric, glycolic, mandelic, tartaric, glyceric or ascorbic acids or salts, amides or esters thereof. By "ion channel blockers" are intended, for example, minoxidil (2,4-diamino-6-piperidinopyrimidine 3-oxide) and derivatives thereof.

The present invention thus also features medicinal compositions containing at least one compound of formula (I), one of its chiral or geometric isomers, or one of its pharmaceutically accepetable salts, or other derivatives thereof.

The pharmaceutical/therapeutic compositions of the present invention, intended especially for treating the aforesaid disease states comprise a pharmaceutically acceptable vehicle, carrier or diluent which is compatible with the mode or regime of administration selected for the given composition, at least one compound of formula (I), one of its chiral or geometric isomers, or one of the salts, etc., thereof.

The administration of the compounds according to the invention can be carried out systemically, enterally, parenterally, topically or ocularly.

For enteral administration, the medicinal/pharmaceutical compositions may be in the form of tablets, hard gelatin capsules, dragees, syrups, suspensions, solutions, elixirs, powders, granules, emulsions or polymeric or lipid microspheres or nanospheres or vesicles which permit a controlled release. For parenteral administration, the compositions may be in the form of solutions or suspensions for perfusion or for injection.

The compounds according to the invention are generally administered at a daily dose of approximately 0.01 mg/kg to 100 mg/kg by body weight, and this at the rate or regime of 1 to 3 doses per diem.

For topical administration, the pharmaceutical compositions based on compounds according to the invention are more particularly intended for treating the skin and the mucosal membranes and can then be provided in the form of ointments, creams, milks, salves, powders, impregnated pads, solutions, gels, sprays, lotions or suspensions. They can also be provided in the form of polymeric or lipid vesicles or nanospheres or microspheres or of polymeric patches and of hydrogels which permit controlled release. These compositions for topical administration can, moreover, be provided either in anhydrous form or in an aqueous form, according to the particular clinical indication.

For ocular administration, they are principally eye washes.

These compositions for a topical or ocular application contain at least one compound of formula (I), or one of its optical or geometric isomers or, alternatively one of its salts, etc., at a concentration preferably ranging from 0.001% to 5% by weight relative to the total weight of the composition.

The compounds of formula (I) according to the invention also find application in the cosmetics field, in particular for body and hair care/hygiene, and especially for the treatment of skins tending to develop acne, for hair regrowth and combating hair loss, for combating the greasy appearance of the skin or the hair, for protecting against the deleterious effects of sunlight or in the treatment of physiologically dry skin, and for preventing and/or for controlling photoinduced or chronologic aging.

For cosmetic applications, the compounds according to the invention can, moreover, be advantageously be used in combination with other compounds displaying a retinoid-type activity, with vitamins D or derivatives thereof, with corticosteroids, with compounds which control free radicals, with α-hydroxy or α-keto acids or derivatives thereof, or alternatively with ion channel blockers, all of these various active agents being as defined above.

The present invention therefore also features cosmetic compositions comprising a cosmetically acceptable vehicle, carrier or diluent which is suitable for topical application, at least one compound of formula (I) or one of its chiral or geometric isomers, or one of its salts, etc. Such cosmetic compositions are advantageously in the form of a cream, milk, lotion, ointment, gel, polymeric or lipid vesicles or nanospheres or microspheres, soap or shampoo.

The concentration of the compound of formula (I) in the cosmetic compositions according to the invention advantageously ranges from 0.001% and 3% by weight relative to the total weight of the composition.

The medicinal and cosmetic compositions according to the invention can, in addition, contain inert or even pharmacodynamically or cosmetically active additives or combinations of these additives, and, especially: wetting agents; depigmenting agents such as hydroquinone, azelaic acid, caffeic acid or kojic acid; emollients; hydrating or moisturizing agents such as glycerol, PEG 400, thiamorpholinone and its derivatives or alternatively urea; anti-seborrhoeic or anti-acne agents such as S-carboxymethylcysteine, S-benzylcysteamine, their salts or derivatives thereof, or benzoyl peroxide; antibiotics such as erythromycin and esters thereof, neomycin, clindamycin and esters thereof, or tetracyclines; anti-fungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids and especially β-carotene; anti-psoriatic agents such as anthralin and its derivatives; and, lastly, eicosa-5,8,11,14-tetraynoic and eicosa-5,8,11-triynoic acids, and esters and amides thereof.

The compositions according to the invention can also contain flavor-enhancing agents, preservatives such as the esters of para-hydroxybenzoic acid, stabilizing agents, moisture-regulating agents, pH-regulating agents, osmotic-pressure-modifying agents, emulsifying agents, UV-A and UV-B screening agents and antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLE 1

Preparation of 4-[3-(1-adamantyl)-4-methoxyphenylethynyl]benzoic acid (a) Synthesis of 3-(1-adamantyl)-4-methoxyphenylacetylene:

4.7 ml (33 mmol) of diisopropylamine and 40 ml of THF were introduced into a three-necked flask under a stream of nitrogen. 20.6 ml (33 mmol) of n-butyllithium (1.6M in hexane) were added dropwise at −78° C. and stirring was carried out at this same temperature for 15 minutes. A solution of 8.5 g (30 mmol) of 3-(1-adamantyl)-4-methoxyacetophenone in 50 ml of THF was then added. After stirring for one hour at −78° C., the solution was treated with 4.8 ml (33 mmol) of diethyl chlorophosphate and the temperature was permitted to return to room temperature. This solution was transferred to a lithium diisopropylamide solution which had been prepared using 9.35 ml (66 mmol) of diisopropylamine and 41 ml (66 mmol) of n-butyllithium (1.6M in hexane) in 90 ml of THF at −78° C. The temperature was permitted to return to room temperature and the mixture was stirred for twelve hours.

The reaction mixture was poured into ice-cold water and the pH was adjusted to 1 with hydrochloric acid (5N). Extraction was carried out with ethyl ether and the organic phase was separated by settling, dried over magnesium sulfate and evaporated.

The residue obtained was purified by chromatography on a silica column eluted with a mixture of dichloromethane and hexane (10/90). After evaporation of the solvents, 4.3 g (54%) of the expected acetylene derivative were collected, which compound had the melting point 121°–2° C.

(b) Synthesis of methyl 4-[3-(1-adamantyl)-4-methoxyphenylethynyl]benzoate:

4.4 ml (7 mmol) of n-butyllithium (1.6M in hexane) were added dropwise at 0° C. to a solution of 1.8 g (6.8 mmol) of 3-(1-adamantyl)-4-methoxyphenylacetylene in 20 ml of THF and the mixture was stirred for thirty minutes at room temperature. The mixture was cooled to 0° C. and 1.05 g (7.7 mmol) of anhydrous $ZnCl_2$ was added and the mixture was stirred for one hour at room temperature.

1.3 g (1.1 mmol) of tetrakis(triphenylphosphine)palladium(0) and 13 ml of THF were introduced into a three-necked flask and a solution of 1.77 g (6.7 mmol) of methyl 4-iodobenzoate was added. Stirring was carried out at room temperature for thirty minutes and the zinc solution prepared above was added dropwise. The reaction mixture was stirred at room temperature for twelve hours, was then poured into a mixture of 80 ml of hydrochloric acid (3N) and ice-cold water and finally extracted with ethyl acetate.

The organic phase was separated by settling, washed with water, dried over magnesium sulfate and evaporated. The residue obtained was purified by chromatography on a silica column eluted with a mixture of hexane and ethyl ether (90/10). After evaporation of the solvents, 970 mg (36%) of the expected methyl ester were collected, which ester had the melting point 197°–8° C.

(c) Synthesis of 4-[3-(1-adamantyl)-4-methoxyphenylethynyl]benzoic acid:

966 mg (2.4 mmol) of the ester prepared in part (b) above and 20 ml of methanolic sodium hydroxide (2N) were introduced into a round-bottomed flask and heating was carried out at reflux for one hour. The reaction mixture was evaporated to dryness, the residue was taken up in water, acidification was carried out with concentrated hydrochloric acid and the solids which had precipitated were filtered.

After recrystallization from ethyl alcohol, 660 mg (71%) of the expected acid were collected, which acid had the melting point 307°–10° C.

EXAMPLE 2

Preparation of 4-[3-(1-adamantyl),4-methoxyethoxymethoxy-phenylethynyl]benzoic acid (a) Synthesis of 3-(1-adamantyl)-1-bromo-4-methoxyethoxymethoxybenzene:

3.8 g (0.13 mol) of sodium hydride (80% in oil) and 50 ml of DMF were introduced into a three-necked flask under a stream of nitrogen, a solution of 40 g (0.13 mol) of 2-(1-adamantyl)-4-bromophenol in 100 ml of DMF was then added dropwise and stirring was carried out until gas evolution has ceased. A solution of 18 ml (0.15 mol) of 2-methoxyethoxymethyl chloride in 20 ml of DMF was then added dropwise and stirring was carried out for four hours at room temperature. The reaction mixture was then poured into water and extracted with ethyl ether and the organic phase was separated by settling, washed with water, dried over magnesium sulphate and evaporated.

The residue was purified by chromatography on a silica column eluted with a mixture of dichloromethane and hexane (50/50). After evaporation of the solvents, 40.1 g (78%) of the expected product are collected, which compound had the melting point 69°–70° C.

(b) Synthesis of 3-(1-adamantyl)-4-methoxyethoxymethoxybenzoic acid:

The compound obtained in part (a) above (28.5 g, 72 mmol) was dissolved in 200 ml of THF. The solution obtained was added dropwise over magnesium (2.4 g, 100 mmol) and iodine crystals. After introduction, heating was carried out at reflux for two hours, cooling was carried out to −78° C. and a stream of $CO_2$ was charged therein for one hour.

The temperature was permitted to increase to room temperature, the reaction mixture is poured into a saturated aqueous ammonium chloride solution and extracted with ethyl ether and the organic phase was separated by settling, dried over magnesium sulfate and evaporated.

The residue obtained was triturated in hexane, filtered and dried. 15.5 g (60%) of the expected acid were collected, which acid had the melting point 115°–6° C.

(c) Synthesis of 3-(1-adamantyl)-4-methoxyethoxymethoxyacetophenone:

15.5 g (43 mmol) of 3-(1-adamantyl)-4-methoxyethoxymethoxybenzoic acid and 300 ml of anhydrous ethyl ether were introduced into a three-necked flask under a stream of nitrogen. 80 ml (0.13 mol) of methyllithium (1.6M in ether) were added dropwise at −20° C. and stirring was then carried out for three hours at room temperature. The reaction mixture was poured into a saturated aqueous ammonium chloride solution and the organic phase was separated by settling, dried over magnesium sulfate and evaporated.

15.4 g (100%) of the expected acetophenone were collected in the form of a slightly yellow oil.

(d) Synthesis of 3-(1-adamantyl)-4-methoxyethoxymethoxyphenylacetylene:

In a manner analogous to Example 1(a) above, from 11.8 g (33 mmol) of 3-(1-adamantyl)-4-methoxyethoxymethoxyacetophenone, 6.3 g (57%) of the expected acetylene were obtained, which acetylene compound had the melting point 81°–2° C.

(e) Synthesis of methyl 4-[3-(1-adamantyl)-4-methoxyethoxymethoxyphenylethynyl]benzoate:

In a manner analogous to Example 1(a) above, by reaction of 1.5 g (4.4 mmol) of 3-(1-adamantyl)-4-methoxyethoxymethoxyphenylacetylene with 1.2 g (4.4 mmol) of methyl 4-iodobenzoate and after purification by chromatography on a silica column eluted with a mixture of dichloromethane and hexane (70/30), 1.5 g (72%) of the expected methyl ester were obtained, which ester had the melting point 92°–3° C.

(f) Synthesis of 4-[3-(1-adamantyl)-4-methoxyethoxymethoxyphenylethynyl]benzoic acid:

In a manner analogous to Example 1(c) above, from 730 mg (1.5 mmol) of the ester prepared in part (e) above, 600 mg (87%) of the expected acid were obtained, which acid had the melting point 203°–4° C.

EXAMPLE 3

Preparation of 4-[3-(1-adamantyl)-4-hydroxyphenylethynyl]benzoic acid (a) Synthesis of methyl 4-[3-(1-adamantyl)-4-hydroxyphenylethynyl]benzoate:

1.3 g (2.7 mmol) of methyl 4-[3-(1-adamantyl)-4-methoxyethoxymethoxyphenylethynyl]benzoate and 50 ml of anhydrous dichloromethane were introduced into a round-bottomed flask and 2.7 ml (2.7 mmol) of boron trichloride (1M in $CH_2Cl_2$) were added dropwise at 0° C.

The reaction mixture was stirred at room temperature for one hour, was poured into water and was extracted with ethyl ether and the organic phase was separated by settling, dried over magnesium sulfate and evaporated.

The residue obtained was triturated in a mixture of hexane and ethyl ether, filtered and dried. 910 mg (91%) of the expected compound were collected, which compound had the melting point 232°–3° C.

(b) Synthesis of 4-[3-(1-adamantyl)-4-hydroxyphenylethynyl]benzoic acid:

In a manner analogous to Example 1(c) above, from 850 mg (2.2 mmol) of methyl 4-[3-(1-adamantyl)-4-hydroxyphenylethynyl]benzoate, 720 mg (88%) of the expected acid were collected, which acid had the melting point 254°–5° C.

EXAMPLE 4

Preparation of 5-[3-(1-adamantyl)-4-hydroxyphenylethynyl]-2-thiophenecarboxylic acid (a) Synthesis of methyl 5-[3-(1-adamantyl)-4-methoxyethoxymethoxyphenylethynyl]-2-thiophenecarboxylate:

In a manner analogous to Example 1(b) above, by reaction of 1.5 g (4.4 mmol) of 3-(1-adamantyl)-4-methoxyethoxymethoxyphenylacetylene with 1 g (4.4 mmol) of methyl 5-bromo-2-thiophene carboxylate, 1.4 g (67%) of the expected methyl ester were obtained in the form of an oil.

(b) Synthesis of methyl 5-[3-(1-adamantyl)-4-hydroxyphenylethynyl]-2-thiophenecarboxylate:

In a manner analogous to Example 3(a) above, from 1.2 g (2.5 mmol) of the ester obtained in part (A) above, 847 mg (86%) of methyl 5-[3-(1-adamantyl)-4-hydroxyphenylethynyl]-2-thiophenecarboxylate were obtained, which compound had the melting point 207°–8° C.

(c) Synthesis of 5-[3-(1-adamantyl)-4-hydroxyphenylethynyl]-2-thiophenecarboxylic acid:

In a manner analogous to Example 1(c) above, from 360 mg (0.9 mmol) of the methyl ester obtained in part (b) above, 300 mg (86%) of 5-[3-(1-adamantyl)-4-hydroxyphenylethynyl]-2-thiophenecarboxylic acid were obtained, which acid had the melting point 249°–50° C.

EXAMPLE 5

Preparation of 5-[3-(1-adamantyl)-4-methoxyphenylethynyl]-2-thiophenecarboxylic acid (a) Synthesis of methyl 5-[3-(1-adamantyl)-4-methoxyphenylethynyl]-2-thiophenecarboxylate:

36 mg (1.2 mmol) of sodium hydride (80% in oil) and 20 ml of DMF were introduced into a three-necked flask under a stream of nitrogen and a solution of 392 mg (1 mmol) of methyl 5-[3-(1-adamantyl)-4-hydroxyphenylethynyl]-2-thiophenecarboxylate in 10 ml of DMF were added dropwise.

The reaction mixture was stirred for thirty minutes, 75 μl (1.2 mmol) of iodomethane were then added and the reaction mixture was stirred at room temperature for four hours. The reaction mixture was then poured into water and extracted with ethyl ether and the organic phase was separated by settling, dried over magnesium sulfate and evaporated.

The residue was triturated in hexane, filtered and dried. 385 mg (95%) of the expected compound were collected, which compound had the melting point 137°–8° C.

(b) Synthesis of 5-[3-(1-adamantyl)-4-methoxyphenylethynyl]-2-thiophenecarboxylic acid:

In a manner analogous to Example 1(c) above, from 370 mg (0.9 mmol) of the methyl ester obtained in part (a) above, 320 mg (90%) of 5-[3-(1-adamantyl)-4-methoxyphenylethynyl]-2-thiophenecarboxylic acid were obtained, which acid had the melting point 244°–5° C.

EXAMPLE 6

Preparation of 2-[3-(1-adamantyl)-4-methoxyphenylethynyl]-4-thiophenecarboxylic acid (a) Synthesis of ethyl 2-[3-(1-Adamantyl)-4-methoxyphenylethynyl]-4-thiophenecarboxylate:

In a manner analogous to Example 1(b) above, by reaction of 3.2 g (12 mmol) of 3-(1-adamantyl)-4-methoxyphenylacetylene with 2.8 g (12 mmol) of ethyl 2-bromo-4-thiophenecarboxylate, there were obtained, after chromatography on a silica column eluted with a mixture of hexane and ethyl acetate, 2.4 g (48%) of the expected ethyl ester with the melting point 88–90° C.

(b) Synthesis of 2-[3-(1-adamantyl)-4-methoxyphenylethynyl]-4-thiophenecarboxylic acid:

In a manner analogous to Example 1(c) above, from 2.3 g (5.4 mmol) of the ester obtained in part (a) above, there was obtained, after recrystallization from ethyl alcohol, 1.8 g (86%) of 2-[3-(1-adamantyl)-4-methoxyphenylethynyl]-4-thiophenecarboxylic acid with the melting point 244°–6° C.

EXAMPLE 7

Preparation of 6-[3-(1-adamantyl)-4-methoxyphenylethynyl]-2-naphthoic acid (a) Synthesis of methyl 6-[3-(1-adamantyl)-4-methoxyphenylethynyl]-2-naphthoate:

In a manner analogous to Example 1(b) above, from 4.5 g (16.9 mmol) of 3-(1-adamantyl)-4-methoxyphenylacetylene and 4.45 g (16.8 mmol) of methyl 6-bromo-2-naphthoate, 3.8 g (50%) of the expected methyl ester were obtained, which ester had the melting point 233°–4° C.

(b) Synthesis of 6-[3-(1-adamantyl)-4-methoxyphenylethynyl]-2-naphthoic acid:

In a manner analogous to Example 1(c) above, from 3.8 g (8.4 mmol) of the ester obtained in part (a) above, 2.2 g (62%) of 6-[3-(1-adamantyl)-4-methoxyphenylethynyl]-2-naphthoic acid were obtained, which acid had the melting point 307°–9° C.

EXAMPLE 8

Preparation of 4-[3-(1-adamantyl)-4-nonyloxyphenylethynyl]benzoic acid (a) Synthesis of methyl 4-[3-(1-adamantyl)-4-nonyloxyphenylethynyl]benzoate:

75 mg (2.6 mmol) of sodium hydride (80% in oil) and 10 ml of DMF were introduced into a three-necked flask under a stream of nitrogen. A solution of 1 g (2.6 mmol) of methyl 4-[3-(1-adamantyl)-4-hydroxyphenylethynyl]benzoate dissolved in 70 ml of DMF was added dropwise and stirring was carried out at room temperature until gas evolution had ceased. 610 µl (3.1 mmol) of 1-iodononane were then added dropwise and stirring was carried out at room temperature for four hours. The reaction mixture was poured into ice-cold water and extracted with ethyl ether and the organic phase was separated by settling, dried over magnesium sulphate and evaporated.

The residue obtained as purified by chromatography on a silica column eluted with a mixture of dichloromethane and heptane (50/50). After evaporation of the solvents, 960 mg (72%) of the expected methyl ester were collected, which ester had the melting point 112°–5° C.

(b) Synthesis of 4-[3-(1-adamantyl)-4-nonyloxyphenylethynyl]benzoic acid:

960 mg (1.9 mmol) of the immediately preceding methyl ester and 25 ml of a 2N methanolic sodium hydroxide solution were introduced into a round-bottomed flask and heating was carried out at reflux for two hours. The reaction mixture was evaporated to dryness, the residue was taken up in water acidifed to pH 1 with hydrochloric acid and extracted with ethyl ether and the organic phase was separated by settling, dried over magnesium sulfate and evaporated.

The residue obtained was triturated in a mixture of dichloromethane and heptane (20/80), filtered and dried. 630 mg (67%) of 4-[3-(1-adamantyl)-4-nonyloxyphenylethynyl] benzoic acid were collected, which acid had the melting point 224°–6° C.

EXAMPLE 9

Preparation of 4-[3-(1-adamantyl)-4-hexyloxyphenylethynyl]benzoic acid (a) Synthesis of methyl 4-[3-(1-adamantyl)-4-hexyloxyphenylethynyl]benzoate:

In a manner analogous to Example 8(a), by reaction of 1 g (2.6 mmol) of methyl 4-[3-(1-adamantyl)-4-hydroxyphenylethynyl]benzoate with 460 µl (3.1 mmol) of 1-iodohexane, 900 mg of the expected methyl ester were obtained, which ester had the melting point 140°–3° C.

(b) Synthesis of 4-[3-(1-adamantyl)-4-hexyloxyphenylethynyl]benzoic acid:

In a manner analogous to Example 8(b), from 900 mg (1.9 mmol) of the preceding methyl ester, 700 mg (80%) of 4-[3-(1-adamantyl)-4-hexyloxyphenylethynyl]benzoic acid were obtained, which acid had the melting point 260°–2° C.

EXAMPLE 10

Preparation of 4-[3-(1-adamantyl)-4-dodecyloxyphenylethynyl]benzoic acid (a) Synthesis of methyl 4-[3-(1-adamantyl)-4-dodecyloxyphenylethynyl]benzoate:

In a manner analogous to Example 8(a), by reaction of 1 g (2.6 mmol) of methyl 4-[3-(1-adamantyl)-4-hydroxyphenylethynyl]benzoate with 750 µl (3.1 mmol) of 1-bromododecane, 1.1 g (77%) of the expected methyl ester was obtained, which ester had the melting point 101°–4° C.

(b) Synthesis of 4-[3-(1-adamantyl)-4-dodecyloxyphenylethynyl]benzoic acid:

In a manner analogous to Example 8(b), from 1.1 g (2 mmol) of the preceding methyl ester, 1 g (93%) of 4-[3-(1-adamantyl)-4-dodecyloxyphenylethynyl]benzoic acid was obtained, which acid had the melting point 225°–7° C.

EXAMPLE 11

Preparation of 4-[3-(1-adamantyl)-4-cyclopropylmethoxyphenylethynyl]benzoic acid (a) Synthesis of methyl 4-[3-(1-Adamantyl)-4-cyclopropylmethoxyphenylethynyl]benzoate:

In a manner analogous to Example 8(a), by reaction of 1 g (2.6 mmol) of methyl 4-[3-(1-adamantyl)-4-hydroxyphenylethynyl]benzoate with 300 µl (3.1 mmol) of bromomethylcyclopropane, 700 mg (61%) of the expected methyl ester were obtained, which ester had the melting point 185°–6° C.

(b) Synthesis of 4-[3-(1-adamantyl)-4-cyclopropylmethoxyphenylethynyl]benzoic acid:

In a manner analogous to Example 8(b), from 700 mg (1.6 mmol) of the preceding methyl ester, 570 mg (84%) of 4-[3-(1-adamantyl)-4-cyclopropylmethoxyphenylethynyl]benzoic acid were obtained, which acid had the melting point 302°–5° C.

EXAMPLE 12

Preparation of 4-[2-hexyloxy-5-(1-adamantyl)-4-hexyloxyphenylethynyl]benzoic acid (a) Synthesis of 2,4-dihydroxy-5-(1-adamantyl)benzaldehyde:

5 g (36.2 mmol) of 2,4-dihydroxybenzaldehyde, 5.8 g (38.1 mmol) of 1-adamantanol of 200 ml of dichloromethane were introduced into a round-bottomed flask. 2 ml of concentrated sulfuric acid were added and the mixture was stirred at room temperature for eight hours. The reaction mixture was evaporated to dryness, the residue was taken up in water, neutralized with sodium bicarbonate and extracted with ethyl ether and the extract was dried over magnesium sulfate and evaporated.

The residue obtained was triturated with a mixture of dichloromethane and heptane (40/60) and the solid was filtered and dried. 6.8 g (69%) of the expected compound were collected, which compound had the melting point 165°–8° C.

(b) Synthesis of 2,4-dihexyloxy-5-(1-adamantyl)benzaldehyde:

1.3 g (35.2 mmol) of sodium hydride (80% in oil) and 50 ml of DMF were introduced into a three-necked flask under a stream of nitrogen. A solution of 4.8 g (17.6 mmol) of 2,4-dihydroxy-5-(1-adamantyl)benzaldehyde dissolved in 70 ml of DMF was added dropwise and stirring was carried out at room temperature until gas evolution has ceased. 6.5 ml (35.2 mmol) of 1-iodohexane were then added dropwise and stirring was carried out at room temperature for four hours.

The reaction mixture was poured into ice-cold water and extracted with ethyl ether and the organic phase was separated by settling, dried over magnesium sulfate and evaporated.

The residue obtained was purified by chromatography on a silica column eluted with dichloromethane. After evaporation of the solvents, 5.5 g (71%) of the expected compound were collected in the form of a slightly blue oil.

(c) Synthesis of 2',2'-dibromo-2,4-dihexyloxy-5-(1-adamantyl)styrene:

5.5 g (12.5 mmol) of 2,4-dihexyloxy-5-(1-adamantyl)benzaldehyde and 100 ml of dichloromethane were introduced into a round-bottomed flask. 8.3 g (25 mmol) of carbon tetrabromide, 6.5 g (25 mmol) of triphenylphosphine and 1.6 g (25 mmol) of zinc powder were added successively and stirring was carried out at room temperature for two hours. The reaction mixture was evaporated and the residue obtained purified by chromatography on a silica column eluted with dichloromethane. 3 g (40%) of the expected compound were collected in the form of a yellow oil.

(d) Synthesis of 2,4-dihexyloxy-5-(1-adamantyl)phenylacetylene:

3 g (5 mmol) of 2',2'-dibromo-2,4-dihexyloxy-5-(1-adamantyl)styrene and 50 ml of THF were introduced into a three-necked flask under a stream of nitrogen. 4 ml (10 mmol) of an n-butyllithium solution (2.5M in hexane) were added dropwise at −78° C. and the temperature was permitted to increase to room temperature for one hour. The reaction mixture was poured into water and extracted with ethyl ether and the organic phase was separated by settling, dried over magnesium sulfate and evaporated.

The residue obtained was purified by chromatography on a silica column eluted with dichloromethane. 1.9 g (86%) of the expected acetylene derivative were collected in the form of a brown oil.

(e) Synthesis of methyl 4-[2-hexyloxy-5-(1-adamantyl)-4-hexyloxyphenylethynyl]benzoate:

1.8 g (4.1 mmol) of 2,4-dihexyloxy-5-(1-adamantyl)phenylacetylene, 1.2 g (4.5 mmol) of methyl 4-iodobenzoate and 15 ml of triethylamine were introduced into a three-necked flask. The reaction mixture was degassed with nitrogen for 15 min, 100 mg of copper iodide and 260 mg (0.37 mmol) of bis(triphenylphosphine)-palladium(II) chloride were added and stirring was carried out at room temperature for twelve hours. The reaction mixture was evaporated to dryness, the residue was taken up in water and ethyl ether and the organic phase was separated by settling, dried over magnesium sulfate and evaporated.

The residue obtained was purified by chromatography on a silica column eluted with a mixture of dichloromethane and heptane (20/80). After evaporation of the solvents, 1.7 g (72%) of the expected methyl ester were collected.

(f) Synthesis of 4-[2-hexyloxy-5-(1-adamantyl)-4-hexyloxyphenylethynyl]benzoic acid:

In a manner analogous to Example 8(b), from 1.7 g (3 mmol) of the preceding methyl ester, 1.5 g (90%) of the expected acid was obtained, which acid had the melting point 213°–4° C.

EXAMPLE 13

Preparation of 4-[3-(1-adamantyl)-4-heptyloxyphenylethynyl]benzoic acid (a) Synthesis of methyl 4-[3-(1-adamantyl)-4-heptyloxyphenylethynyl]benzoate:

In a manner analogous to Example 8(a), by reaction of 500 mg (1.3 mmol) of methyl 4-[3-(1-adamantyl)-4-hydroxyphenylethynyl]benzoate with 250 µl (1.56 mmol) of 1-bromoheptane, 500 mg (82%) of the expected methyl ester were obtained.

(b) Synthesis of 4-[3-(1-adamantyl)-4-heptyloxyphenylethynyl]benzoic acid:

In a manner analogous to Example 8(b), from 500 mg (1.07 mmol) of the preceding methyl ester, 350 mg (70%) of 4-[3-(1-adamantyl)-4-heptyloxyphenylethynyl]benzoic acid were obtained, which acid had the melting point 256°–7° C.

EXAMPLE 14

Preparation of
6-[3-(1-adamantyl)-4-methoxyethoxymethoxyphenylethynyl]nicotinic acid (a) Synthesis of methyl 6-[3-(1-adamantyl)-4-methoxyethoxymethoxyphenylethynyl]nicotinate:

In a manner analogous to Example 12(e), by reaction of 2.5 g (7.4 mmol) of 3-(1-adamantyl)-4-methoxyethoxymethoxyphenylacetylene with 1.93 g (7.4 mmol) of methyl 6-iodonicotinate, 1.98 g (56%) of the expected methyl ester was obtained, which ester had the melting point 86°–7° C.
(b) Synthesis of 6-[3-(1-adamantyl)-4-methoxyethoxymethoxyphenylethynyl]nicotinic acid:

In a manner analogous to Example 8(b), from 1.5 g (3.1 mmol) of the preceding methyl ester, 1.4 g (95%) of the expected acid was obtained, which acid had the melting point 204°–5° C.

EXAMPLE 15

Preparation of 4-[2-methoxy-5-(1-adamantyl)
-4-methoxyphenylethynyl]benzoic acid (a) Synthesis of 2,4-dimethoxy-5-(1-adamantyl)benzaldehyde:

In a manner analogous to Example 12(b), by reaction of 1.1 g (3.8 mmol) of 2,4-dihydroxy-5-(1-adamantyl)benzaldehyde with 620 µl (9.8 mmol) of methyl iodide, 1 g (87%) of the expected compound was obtained, which compound had the melting point 152°–4° C.
(b) Synthesis of 2',2'-dibromo-2,4-dimethoxy-5-(1-adamantyl)styrene:

In a manner analogous to Example 12(c), from 1.8 g (6mmol) of the preceding aldehyde, 1.2 g (44%) of 2',2'-dibromo-2,4-dimethoxy-5-(1-adamantyl)styrene was obtained, which compound had the melting point 176°–8° C.
(c) Synthesis of 2,4-dimethoxy-5-(1-adamantyl)phenylacetylene:

In a manner analogous to Example 12(d), from 1.2 g (2.6 mmol) of the preceding product, 300 mg (38%) of the expected acetylene derivative were obtained, which derivative had the melting point 210°–3° C.
(d) Synthesis of methyl 4-[2-methoxy-5-(1-adamantyl)-4-methoxyphenylethynyl]benzoate:

In a manner analogous to Example 12(e) by reaction of 300 mg (1 mmol) of 2,4-dimethoxy-5-(1-adamantyl)phenylacetylene with 265 mg (1 mmol) of methyl-4-iodobenzoate, 350 mg (80%) of the expected methyl ester were obtained, which ester had the melting point 186°–8° C.
(e) Synthesis of 4-[2-methoxy-5-(1-adamantyl)-4-methoxyphenylethynyl]benzoic acid:

In a manner analogous to Example 8(b), from 350 mg (0.8 mmol) of the preceding methyl ester, 290 mg (85%) of 4-[2-methoxy-5-(1-adamantyl)-4-methoxyphenylethynyl] benzoic acid were obtained, which acid had the melting point 274°–8° C.

EXAMPLE 16

Preparation of
4-[2-methoxyethoxymethoxy-5-(1-adamantyl)-4-methoxyethoxymethoxyphenylethynyl]benzoic acid (a) Synthesis of 2,4-dimethoxyethoxymethoxy-5-(1-adamantyl)benzaldehyde:

In a manner analogous to Example 12(b), by reaction of 25 g (92 mmol) of 2,4-dihydroxy-5-(1-adamantyl)benzaldehyde with 26.2 ml (230 mmol) of methoxyethoxymethyl chloride, 31 g (75%) of the expected compound were obtained in the form of a yellow oil.
(b) Synthesis of 2',2'-dibromo-2,4-dimethoxyethoxymethoxy-5-(1-adamantyl)styrene:

In a manner analogous to Example 12(c), from 4.5 g (10 mmol) of the preceding aldehyde, 5.5 g (90%) of 2',2'-dibromo-2,4-dimethoxyethoxymethoxy-5-(1-adamantyl)styrene were obtained in the form of a brown oil.
(c) Synthesis of 2,4-dimethoxyethoxymethoxy-5-(1-adamantyl)phenylacetylene:

In a manner analogous to Example 12(d), from 5.5 g (9.1 mmol) of the preceding product, 900 mg (23%) of the expected acetylene derivative were obtained in the form of a colorless oil.
(d) Synthesis of methyl 4-[2-methoxyethoxymethoxy-5-(1-adamantyl)-4-methoxyethoxymethoxyphenylethynyl]benzoate:

In a manner analogous to Example 12(e), by reaction of 900 mg (2 mmol) of 2,4-dimethoxy-ethoxymethoxy-5-(1-adamantyl)phenylacetylene with 530 mg (2 mmol) of methyl 4-iodobenzoate, 950 mg (81%) of the expected methyl ester were obtained in the form of a brown oil.
(e) Synthesis of 4-[2-methoxyethoxymethoxy-5-(1-adamantyl)-4-methoxyethoxymethoxyphenylethynyl]benzoic acid:

In a manner analogous to Example 8(b), from 950 mg (1.6 mmol) of the preceding methyl ester, 730 mg (79%) of 4-[2-methoxyethoxymethoxy-5-(1-adamantyl)-4-methoxyethoxymethoxyphenylethynyl]benzoic acid were obtained, which acid had the melting point 131°–5° C.

EXAMPLE 17

Preparation of
4-[2-methoxy-5-(1-adamantyl)-4-methoxyethoxymethoxyphenylethynyl]benzoic acid (a) Synthesis of 2-hydroxy-4-methoxyethoxymethoxy-5-(1-adamantyl)benzaldehyde:

5 g (11.2 mmol) of 2,4-dimethoxyethoxymethoxy-5-(1-adamantyl)benzaldehyde and 100 ml of dichloromethane were introduced into a three-necked flask under a stream of nitrogen. 11.2 ml of a boron trichloride solution (1M in hexane) were added dropwise at −78° C. and stirring was carried out at the same temperature for 18 hours. The reaction mixture was poured into ice-cold water and the organic phase was separated by settling, dried over magnesium sulfate and evaporated.

The residue obtained was purified by chromatography on a silica column eluted with dichloromethane. After evaporation of the solvents, 3.1 g (77%) of 2-hydroxy-4-methoxyethoxymethoxy-5-(1-adamantyl)benzaldehyde were collected, which compound had the melting point 102°–4° C.
(b) Synthesis of 2-methoxy-4-methoxyethoxymethoxy-5-(1-adamantyl)benzaldehyde:

In a manner analogous to Example 12(b), by reaction of 2.9 g (8 mmol) of the preceding aldehyde derivative with 550 µl (8.8 mmol) of methyl iodide, 2.1 g (70%) of the expected compound were obtained, which compound had the melting point 48°–50° C.

(c) Synthesis of 2',2'-dibromo-2-methoxy-4-methoxyethoxymethoxy-5-(1-adamantyl)styrene:

In a manner analogous to Example 12(c), from 2.1 g (5.6mmol) of the preceding aldehyde, 2 g (67%) of 2',2'-dibromo-2-methoxy-4-methoxyethoxymethoxy-5-(1-adamantyl)styrene were obtained in the form of a colorless oil.

(d) Synthesis of 2-methoxy-4-methoxyethoxymethoxy-5-(1-adamantyl)phenylacetylene:

In a manner analogous to Example 12(d), from 2 g (3.8 mmol) of the preceding product, 1.3 g (93%) of the expected acetylene derivative were obtained in the form of a colorless oil.

(e) Synthesis of methyl 4-[2-methoxy-5-(1-adamantyl)-4-methoxyethoxymethoxyphenylethynyl]benzoate:

In a manner analogous to Example 12(e), by reaction of 1.3 g (3.5 mmol) of 2-methoxy-4-methoxyethoxymethoxy-5-(1-adamantyl)phenylacetylene with 920 mg (3.5 mmol) of methyl 4-iodobenzoate, 1.3 g (73%) of the expected methyl ester was obtained, which ester had the melting point 152°–5° C.

(f) Synthesis of 4-[2-methoxy-5-(1-adamantyl)-4-methoxyethoxymethoxyphenylethynyl benzoic acid:

In a manner analogous to Example 8(b), from 1.3 g (2.6 mmol) of the preceding methyl ester, 1.05 g (83%) of 4-[2-methoxy-5-(1-adamantyl)-4-methoxyethoxymethoxyphenylethynyl]benzoic acid was obtained, which acid had the melting point 210°–1° C.

EXAMPLE 18

Preparation of 4-[3-(1-adamantyl)-4-benzyloxyphenylethynyl]benzoic acid (a) Synthesis of methyl 4-[3-(1-adamantyl)-4-benzyloxyphenylethynyl]benzoate:

In a manner analogous to Example 8(a), by reaction of 1.1 g (2.8 mmol) of methyl 4-[3-(1-adamantyl)-4-hydroxyphenylethynyl]benzoate with 410 µl (3.4 mmol) of benzyl bromide, 800 mg (57%) of the expected methyl ester were obtained, which ester had the melting point 168°–9° C.

(b) Synthesis of 4-[3-(1-adamantyl)-4-benzyloxyphenylethynyl]benzoic acid:

In a manner analogous to Example 8(b), from 800 mg (1.68 mmol) of the preceding methyl ester, 690 mg (88%) of 4-[3-(1-adamantyl)-4-benzyloxyphenylethynyl]benzoic acid were obtained, which acid had the melting point 288°–9° C.

EXAMPLE 19

Preparation of 4-[3-(1-adamantyl) -4-methoxyethoxymethoxyphenylethynyl]benzaldehyde 3 g (8.8 mmol) of 3-(1-adamantyl)-4-methoxyethoxymethoxyphenylacetylene, 1.8 g (9.7 mmol) of 4-bromobenzaldehyde and 50 ml of triethylamine were introduced into a three-necked flask. The reaction mixture was degassed with nitrogen for 15 min, 160 mg (1.7 mmol) of palladium(II) acetate and 350 mg (1.3 mmol) of triphenylphosphine were added and stirring was carried out at room temperature for twelve hours. The reaction mixture was evaporated to dryness, the residue was taken up in water and ethyl ether and the organic phase was separated by settling, dried over magnesium sulfate and evaporated.

The residue obtained was purified by chromatography on a silica column eluted with a mixture of ethyl acetate and heptane (10/90). After evaporation of the solvents, 1.39 g (34%) of 4-[3-(1-adamantyl)-4-methoxyethoxymethoxyphenylethynyl]benzaldehyde was collected, which compound had the melting point 120°–1° C.

EXAMPLE 20

Preparation of 4-[3-(1-adamantyl)-4-methoxyethoxymethoxyphenylethynyl]benzenemethanol 740 mg (1.6 mmol) of 4-[3-(1-adamantyl)-4-methoxyethoxymethoxyphenylethynyl]benzaldehyde were introduced into 40 ml of a mixture of THF and methanol (50/50) in a round-bottomed flask. 32 mg (0.8 mmol) of sodium borohydride were introduced in small amounts at 5° C. and the temperature was permitted to increase to room temperature. The reaction mixture was poured into water and extracted with ethyl acetate and the organic phase was separated by settling, dried over magnesium sulfate and evaporated.

The residue obtained was purified by chromatography on a silica column eluted with a mixture of ethyl acetate and heptane (20/80). After evaporation of the solvents, 440 mg (60%) of 4-[3-(1-adamantyl)-4-methoxyethoxymethoxyphenylethynyl]benzenemethanol were collected, which compound had the melting point 103°–4° C.

EXAMPLE 21

Preparation of 4-[3-(1-adamantyl) -4-methoxyethoxymethoxy-phenylethynyl]benzyl acetate 300 mg (0.7 mmol) of the alcohol obtained in the preceding example, 30 ml of dichloromethane and 230 µl (1.6 mmol) of triethylamine were introduced into a three-necked flask under a stream of nitrogen. 60 µl (0.8 mmol) of acetyl chloride were added and stirring was carried out at room temperature for two hours. The reaction mixture was poured into water and extracted with dichloromethane and the organic phase was separated by settling, dried over magnesium sulfate and evaporated. The residue obtained was crystallized from heptane and, after filtration, 190 mg (64%) of 4-[3-(1-adamantyl)-4-methoxyethoxymethoxyphenylethynyl]benzyl acetate were collected, which acetate had the melting point 83°–4° C.

EXAMPLE 22

Preparation of 4-[3-(1-adamantyl)-4-methoxyethoxymethoxy-phenylethynyl]phenyl acetate In a manner analogous to Example 12(e), by reaction of 2 g (5.9 mmol) of 3-(1-adamantyl)-4-methoxyethoxymethoxyphenylacetylene with 1.6 g (5.9 mmol) of 4-bromophenyl acetate, 1.2 g (43%) of the expected acetate were obtained, which acetate had the melting point 92°–3° C.

EXAMPLE 23

Preparation of 4-[3-(1-adamantyl)-4-methoxyethoxymethoxyphenylethynyl]phenol

In a manner analogous to Example 8(b), from 840 mg (1.8 mmol) of 4-[3-(1-adamantyl)-4-methoxyethoxymethoxyphenylethynyl]phenyl acetate, 710 mg (92%) of the expected phenol derivative were obtained, which derivative has the melting point 122°–3° C.

EXAMPLE 24

Preparation of 4-[3-(1-adamantyl)-4-methoxyethoxymethoxyphenylethynyl]phenoxyethylmorpholine 380 mg (0.9 mmol) of 4-[3-(1-adamantyl)-4-methoxyethoxymethoxyphenylethynyl]phenol, 200 mg of 4-(2-chloroethyl)morpholine hydrochloride, 300 mg (2 mmol) of potassium carbonate, 3 mg of potassium iodide and 50 ml of 2-butanone were introduced into a round-bottomed flask. The reaction mixture was heated at reflux for eight hours and was evaporated to dryness, the residue was taken up in water and ethyl acetate and the organic phase was separated by settling, dried over magnesium sulfate and evaporated.

The residue obtained was triturated in heptane and filtered. 330 mg (69%) of 4-[3-(1-adamantyl)-4-methoxyethoxymethoxyphenylethynyl]phenoxyethylmorpholine were collected, which compound had the melting point 168°–9° C.

EXAMPLE 25

Preparation of 4-[3-(1-adamantyl)-4-methoxyethoxymethoxyphenylethynyl]benzamide (a) Synthesis of 4-[3-(1-adamantyl)-4-methoxyethoxymethoxyphenylethynyl]benzoyl chloride:

A solution of 3.14 g (6.8 mmol) of 4-[3-(1-adamantyl)-4-methoxyethoxymethoxyphenylethynyl]benzoic acid in 100 ml of anhydrous dichloromethane was introduced into a round-bottomed flask, 1.4 ml (6.8 mmol) of dicyclohexylamine was added and stirring was carried out for one hour. 500 µl (6.8 mmol) of thionyl chloride were then added and stirring was carried out for one hour. Evaporation was carried out to dryness, the residue was taken up in anhydrous ethyl ether, the dicyclohexylamine salt was filtered and the filtrate was evaporated. 3.3 g (100%) of the crude acid chloride were collected, which chloride was used as is in the continuation of the synthesis to follow.

(b) Synthesis of 4-[3-(1-adamantyl)-4-methoxyethoxymethoxyphenylethynyl]benzamide:

500 µl (9.1 mmol) of an aqueous ammonia solution (32%) and 20 ml of THF were introduced into a round-bottomed flask. A solution of 1.1 g (2.3 mmol) of 4-[3-(1-adamantyl)-4-methoxyethoxymethoxyphenylethynyl]benzoyl chloride dissolved in 30 ml of THF was added dropwise and stirring was carried out at room temperature for three hours. The reaction mixture was poured into water and extracted with ethyl acetate and the organic phase was separated by settling, dried over magnesium sulfate and evaporated.

The residue obtained was purified by chromatography on a silica column eluted with a mixture of dichloromethane and methanol (98/2). After evaporation of the solvents, 550 mg (53%) of the expected amide were collected, which amide had the melting point 206°–7° C.

EXAMPLE 26

Preparation of N-ethyl-4-[3-(1-adamantyl)-4-methoxyethoxymethoxyphenylethynyl]benzamide In a manner analogous to Example 25(b), by reaction of 1.1 g (2.3 mmol) of 4-[3-(1-adamantyl)-4-methoxyethoxymethoxyphenylethynyl]benzoyl chloride with 600 µl (9.1 mmol) of ethylamine (70%), 520 mg (47%) of the expected ethylamide were obtained, which compound had the melting point 141°–2° C.

EXAMPLE 27

Preparation of 4-[3-(1-adamantyl)-4-methoxyethoxymethoxyphenylethynyl]benzoic acid morpholide In a manner analogous to Example 25(b), by reaction of 1.1 g (2.3 mmol) of 4-[3-(1-adamantyl)-4-methoxyethoxymethoxyphenylethynyl]benzoyl chloride with 600 µl (6.8 mmol) of morpholine, 930 mg (44%) of the expected amide were obtained, which amide had the melting point 142°–3° C.

EXAMPLE 28

Preparation of 2-hydroxy-4-[3-(1-adamantyl)-4-methoxyethoxymethoxyphenylethynyl]benzoic acid (a) Synthesis of methyl 2-hydroxy-4-[3-(1-adamantyl)-4-methoxyethoxymethoxyphenylethynyl]benzoate:

In a manner analogous to Example 12(e), by reaction of 690 mg (1.9 mmol) of 3-(1-adamantyl)-4-methoxyethoxymethoxyphenylacetylene with 530 mg (1.9 mmol) of methyl 2-hydroxy-4-iodobenzoate, 490 mg (52%) of the expected methyl ester were obtained, which ester had the melting point 96°–7° C.

(b) Synthesis of 2-hydroxy-4-[3-(1-adamantyl)-4-methoxyethoxymethoxyphenylethynyl]benzoic acid:

In a manner analogous to Example 8(b), from 500 mg (1 mmol) of methyl 2-hydroxy-4-[3-(1-adamantyl)-4-methoxyethoxymethoxyphenylethynyl]benzoate, 360 mg (74%) of 2-hydroxy-4-[3-(1-adamantyl)-4-methoxyethoxymethoxy-phenylethynyl]benzoic acid were obtained, which acid had the melting point 186°–7° C.

EXAMPLE 29

Preparation of 4-[3-(1-adamantyl)-4-(6-hydroxyhexyloxy)phenylethynyl]benzoic acid (a) Synthesis of methyl 4-[3-(1-adamantyl)-4-(6-hydroxyhexyloxy)phenylethynyl]benzoate:

2 g (5.1 mmol) of methyl 4-[3-(1-adamantyl)-4-hydroxyphenylethynyl]benzoate, 1.1 ml (8.3 mmol) of 6-bromo-1-hexanol, 1.2 g (8.8 mmol) of potassium carbonate, 20 mg of potassium iodide and 100 ml of 2-butanone were introduced into a round-bottomed flask. The reaction mixture was heated at reflux for twelve hours and was evaporated to dryness, the residue was taken up in water and ethyl acetate and the organic phase was separated by settling, dried over magnesium sulfate and evaporated.

The residue obtained was purified by chromatography on a silica column eluted with a mixture of ethyl acetate and heptane (50/50). After evaporation of the solvents, 1.2 g (47%) of the expected compound was collected, which compound had a melting point 141°–2° C.

(b) Synthesis of 4-[3-(1-adamantyl)-4-(6-hydroxyhexyloxy)phenylethynyl]benzoic acid:

In a manner analogous to Example 8(b), from 400 mg (0.8 mmol) of the preceding methyl ester, 330 mg (85%) of 4-[3-(1-adamantyl)-4-(6-hydroxyhexyloxy)phenylethynyl] benzoic acid were collected, which acid had the melting point 228°9° C.

EXAMPLE 30

Preparation of 4-[3-(1-adamantyl)-4-(6-methoxyhexyloxy)phenylethynyl]benzoic acid (a) Synthesis of methyl 4-[3-(1-adamantyl)-4-(6-methoxyhexyloxy)phenylethynyl]benzoate:

390 mg (0.8 mmol) of methyl 4-[3-(1-adamantyl)-4-(6-hydroxyhexyloxy)phenylethynyl]benzoate, 10 ml of toluene and 200 µl of a 50% sodium hydroxide solution were introduced into a round-bottomed flask. 20 mg (5.4 mmol) of tetrabutylammonium iodide and 100 µl (0.9 mmol) of dimethyl sulfate were added and stirring was carried out at room temperature for four hours. The reaction mixture was poured into water and extracted with ethyl acetate and the organic phase was separated by settling, dried over magnesium sulphate and evaporated.

The residue obtained was purified by chromatography on a silica column eluted with a mixture of ethyl acetate and heptane (10/90). After evaporation of the solvents, 60 mg (15%) of the expected methyl ester were collected, which ester had the melting point 112°–3° C.

(b) Synthesis of 4-[3-(1-adamantyl)-4-(6-methoxyhexyloxy)phenylethynyl]benzoic acid:

In a manner analogous to Example 8(b), from 170 mg (0.34 mmol) of the preceding methyl ester, 100 mg (61%) of 4-[3-(1-adamantyl)-4-(6-methoxyhexyloxy)phenylethynyl] benzoic acid were collected, which acid had the melting point 241°–2° C.

EXAMPLE 31

Preparation of 4-[[3-(1-adamantyl)-4-[2-(4-morpholino)ethoxy]phenylethynyl]]benzoic acid (a) Synthesis of methyl 4-[[3-(1-adamantyl)-4-[2-(4-morpholino)ethoxy]phenylethynyl]]benzoate:

In a manner analogous to Example 29(a), by reaction of 750 mg (1.9 mmol) of methyl 4-[3-(1-adamantyl)-4-hydroxyphenylethynyl]benzoate with 430 mg (2.3 mmol) of 4-(2-chloroethyl)morpholine hydrochloride, 540 mg (56%) of the expected methyl ester were obtained, which ester had the melting point 208-9° C.

(b) Synthesis of 4-[[3-(1-adamantyl)-4-[2-(4-morpholino)ethoxy]phenylethynyl]]benzoic acid:

In a manner analogous to Example 8(b), from 540 mg (1 mmol) of the preceding methyl ester, 410 mg (79%) of 4-[3-(1-adamantyl)-4-[2-(4-morpholino)ethoxy]phenylethynyl]benzoic acid were collected, which acid had the melting point 271°–2° C.

EXAMPLE 32

Preparation of 4-[3-(1-adamantyl)-4-(5-carbamoylpentyloxy)phenylethynyl]benzoic acid (a) Synthesis of methyl 4-[3-(1-adamantyl)-4-(5-carbamoylpentyloxy)phenylethynyl]benzoate:

In a manner analogous to Example 29(a), by reaction of 772 mg (2 mmol) of methyl 4-[3-(1-adamantyl)- 4-hydroxyphenylethynyl]benzoate with 584 mg (3 mmol) of 6-bromohexanamide, 264 mg (26%) of the expected methyl ester were obtained, which ester had the melting point 198°–200° C.

(b) Synthesis of 4-[3-(1-adamantyl)-4-(5-carbamoylpentyloxy)phenylethynyl]benzoic acid:

In a manner analogous to Example 8(b), from 254 mg (0.5 mmol) of the preceding methyl ester, 100 mg (40%) of 4-[3-(1-adamantyl)-4-(5-carbamoylpentyloxy)phenylethynyl]benzoic acid were collected, which acid had the melting point 269°–70° C.

EXAMPLE 33

Preparation of 4-[3-(1-adamantyl)-4-(3-hydroxypropyloxy)phenylethynyl]benzoic acid (a) Synthesis of methyl 4-[3-(1-adamantyl -4-(3-hydroxypropyloxy)phenylethynyl]benzoate:

In a manner analogous to Example 29(a), by reaction of 773 mg (2 mmol) of methyl 4-[3-(1-adamantyl)-4-hydroxyphenylethynyl]benzoate with 417 mg (3 mmol) of 3-bromo-1-propanol, 683 mg (77%) of the expected methyl ester were obtained, which ester had the melting point 180°–2° C.

(b) Synthesis of 4-[3-(1-adamantyl) -4-(3-hydroxypropyloxy)phenylethynyl]benzoic acid:

In a manner analogous to Example 8(b), from 678 mg (1.52 mmol) of the preceding methyl ester, 600 mg (92%) of 4-[3-(1-adamantyl)-4-(3-hydroxypropyloxy)phenylethynyl] benzoic acid were collected, which acid had the melting point 290°–2° C.

EXAMPLE 34

Preparation of 4-[3-(1-adamantyl)-4-(3-hydroxy-2-methylpropyloxy)phenylethynyl]benzoic acid (a) Synthesis of methyl 4-[3-(1-adamantyl -4-(3-hydroxy-2-methylpropyloxy)phenylethynyl]benzoate:

In a manner analogous to Example 29(a), by reaction of 773 mg (2 mmol) of methyl 4-[3-(1-adamantyl)-4-hydroxyphenylethynyl]benzoate with 477 mg (3 mmol) of 3-bromo-2-methyl-1-propanol, 250 mg (27%) of the expected methyl ester were obtained, which ester had the melting point 174°–6° C.

(b) Synthesis of 4-[3-(1-adamantyl)-4-(3-hydroxy-2-methylpropyloxy) phenylethynyl]benzoic acid:

In a manner analogous to Example 8(b), from 228 mg (0.5 mmol) of the preceding methyl ester, 166 mg (72%) of 4-[3-(1-adamantyl)-4-(3-hydroxy-2-methylpropyloxy)phenylethynyl]benzoic acid were collected, which acid had the melting point 260°–2° C.

EXAMPLE 35

Preparation of
4-[3-(1-adamantyl)-4-[(2,2-dimethyl1,3-dioxolan-4-methoxy)phenylethynyl]benzoic acid (a) Synthesis of methyl 4-[3-(1-adamantyl)-4-[(2,2-dimethyl-1,3-dioxolan-4-methoxy)phenylethynyl]benzoate:

1.22 g (3.1 mmol) of methyl 4-[3-(1-adamantyl)-4-hydroxyphenylethynyl]benzoate in 25 ml of DMF was treated successively with 523 mg of potassium carbonate and 1.08 g (3.8 mmol) of 3-tosyloxy-1,2-propanediol acetonide. The reaction mixture was stirred at room temperature for four hours and then heated at 80° C. for sixteen hours.

After the usual treatment, the residue obtained was triturated in heptane, filtered and dried. 862 mg (55%) of the expected methyl ester were collected, which ester had the melting point 203°–4° C.

(b) Synthesis of 4-[3-(1-adamantyl)-4-[(2,2-dimethyl-1,3-dioxolan-4-methoxy)phenylethynyl]benzoic acid:

In a manner analogous to Example 8(b), from 404 mg (0.8 mmol) of the preceding methyl ester, 341 mg (87%) of 4-[3-(1-adamantyl)-4-[(2,2-dimethyl1,3-dioxolan-4-methoxy)phenylethynyl]benzoic acid were collected, which acid had the melting point 272°–4° C.

EXAMPLE 36

Preparation of
4-[3-(1-adamantyl)-4-(2,3-dihydroxypropyloxy)phenylethynyl]benzoic acid (a) Synthesis of methyl. 4-[3-(1-adamantyl)-4-(2,3-dihydroxypropyloxy)phenylethynyl]benzoate:

450 mg (0.9 mmol) of methyl 4-[3-(1-adamantyl)-4-[(2,2-dimethyl1,3-dioxolan-4-yl)methoxy]phenyl-ethynyl]benzoate were placed in suspension in 10 ml of a formic acid solution (40%) and heated at 100° C. for three days. The reaction mixture was poured into water and extracted with ethyl acetate and the organic phase was separated by settling, dried over magnesium sulphate and evaporated. The residue obtained was purified by chromatography on a silica column eluted with dichloromethane. 220 mg (53%) of the expected methyl ester were collected, which ester had the melting point 202°–3° C.

(b) Synthesis of 4-[3-(1-adamantyl)-4-(2,3-dihydroxypropyloxy)phenylethynyl]benzoic acid:

In a manner analogous to Example 8(b), from 205 mg (0.44 mmol) of the preceding methyl ester, 153 mg (78%) of 4-[3-(1-adamantyl)-4-(2,3-dihydroxypropyloxy)phenylethynylbenzoic acid were collected, which acid had the melting point 300°–2° C.

EXAMPLE 37

In this example, various specific formulations based on the compounds according to the invention are illustrated.

(A) ORAL ROUTE:

(a) 0.2 g Tablet:

| | | |
|---|---|---|
| (i) | Compound prepared in Example 1 | 0.001 g |
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vi) | Magnesium stearate | 0.005 g |

(b) Oral (drinkable) suspension in 10 ml ampoules:

| | | |
|---|---|---|
| (i) | Compound of Example 2 | 0.05 g |
| (ii) | Glycerol | 1.000 g |
| (iii) | 70% Sorbitol | 1.000 g |
| (iv) | Sodium saccharin | 0.010 g |
| (v) | Methyl para-hydroxybenzoate | 0.080 g |
| (vi) | Flavoring q.s. | 0.080 g |
| (vii) | Purified water q.s. for | 10 mil |

(B) TOPICAL ROUTE:

(a) ointment:

| | | |
|---|---|---|
| (i) | Compound of Example 1 | 0.020 g |
| (ii) | Isopropyl myristate | 81.700 g |
| (iii) | Fluid paraffin oil | 9.100 g |
| (iv) | Silica ("Aerosil 200" marketed by Degussa) | 9.180 g |

(b) ointment:

| | | |
|---|---|---|
| (i) | Compound of Example 2 | 0.300 g |
| (ii) | Pharmaceutical-grade white petroleum jelly q.s. for | 100 g |

(c) Nonionic water-in-oil cream:

| | | |
|---|---|---|
| (i) | Compound of Example 3 | 0.100 g |
| (ii) | Mixture of emulsified lanolin alcohols, waxes and oils ("Anhydrous Eucerin" marketed by BDF) | 39.900 g |
| (iii) | Methyl para-hydroxybenzoate | 0.075 g |
| (iv) | Propyl para-hydroxybenzoate | 0.075 g |
| (v) | Sterile demineralized water q.s. for | 100 g |

(d) Lotion:

| | | |
|---|---|---|
| (i) | Compound of Example 1 | 0.100 g |
| (ii) | Polyethylene glycol (PEG 400) | 69.900 g |
| (iii) | 95% Ethanol | 30.000 g |

(e) Hydrophobic ointment:

| | | |
|---|---|---|
| (i) | Compound of Example 3 | 0.300 g |
| (ii) | Isopropyl myristate | 36.400 g |
| (iii) | Silicone oil ("Rhodorsil 47 V 300" marketed by Rhône-Poulenc) | 36.400 g |
| (iv) | Beeswax | 13.600 g |
| (v) | Silicone oil ("Abil 300.000 cst" marketed by Goldschmidt) q.s. for | 100 g |

(f) Nonionic oil-in-water cream:

| | | |
|---|---|---|
| (i) | Compound of Example 4 | 0.500 g |
| (ii) | Cetyl alcohol | 4.000 g |
| (iii) | Glyceryl monostearate | 2.500 g |
| (iv) | PEG 50 stearate | 2.500 g |
| (v) | Karite butter | 9.200 g |
| (vi) | Propylene glycol | 2.000 g |
| (vi) | Methyl para-hydroxybenzoate | 0.075 g |
| (viii) | Propyl para-hydroxybenzoate | 0.075 g |
| (ix) | Sterile demineralized water q.s. for | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An adamantyl-substituted polycyclic acetylene compound having the structural formula (I):

(I)

in which X is a hydrogen atom or a halogen atom; $R_1$ is a hydrogen atom, a —$CH_3$ radical, a —$CH_2$—O—$R_4$ radical, a —$CH_2$—O—CO—$R_5$ radical, an —O—$R_6$ radical, an —O—$(CH_2)_m$—$(CO)_n$—$R_7$ radical, a —$(CH_2)_p$—CO—$R_8$ radical, a —$(CH_2)_p$—CO—O—$R_9$ radical or an —S(O)$_p$—$R_{10}$ radical, wherein m, n and p and the radicals $R_4$ to $R_{10}$ are as defined below; Ar is a radical selected from among those of the following formulae (a)–(f):

(a)

(b)

(c)

(d)

(e)

(f)

wherein $R_{10}$ and $R_{11}$ are as defined below; $R_2$ is a hydrogen atom or a halogen atom, a linear or branched alkyl radical having from 1 to 20 carbon atoms, an —O—$CH_2$—O—$CH_2$—$CH_2$—O—$CH_3$ radical or an —O—$R_{13}$ radical, wherein $R_{13}$ is as defined below; $R_3$ is an —O—$CH_2$—O—$CH_2$—$CH_2$—O—$CH_3$ radical, a —(Y)$_n$—$(CH_2)_q$—$R_{14}$ radical, a —$(CH_2)_m$—Y—$(CH_2)_q$—$R_{14}$ radical or a —CH=CH—$(CH_{2t}$—$R_4$, radical, wherein m, n, q and t and the Y and $R_{14}$ radicals are as defined below; m is an integer equal to 1, 2 or 3, n is an integer equal to 0 or 1, p is an integer equal to 0, 1, 2 or 3, q is an integer ranging from 0 to 12, inclusive, and t is an integer ranging from 0 to 10, inclusive; $R_4$ is a hydrogen atom or a lower alkyl radical; $R_5$ is a lower alkyl radical; $R_6$ is a hydrogen atom or a lower alkyl radical; $R_7$ is a lower alkyl radical or a heterocycle; $R_8$ is a hydrogen atom, a lower alkyl radical, or a radical:

in which R' and R", which may be identical or different, are each a hydrogen atom, a lower alkyl radical, a mono- or polyhydroxyalkyl radical, an optionally substituted aryl radical or an amino acid or peptide or sugar residue, with the proviso that R' and R" may together form, with the nitrogen atom from which they depend, a nitrogen-containing heterocycle; $R_9$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_{10}$ is a hydrogen atom or a lower alkyl radical; $R_{11}$ is a hydrogen atom, a halogen atom, a lower alkyl radical, a hydroxyl radical, or an —O—$R_{12}$ or —O—CO$R_{12}$ radical, wherein $R_{12}$ is as defined below; $R_{12}$ is a lower alkyl radical; $R_{13}$ is a hydrogen atom or a linear or branched alkyl radical having from 1 to 20 carbon atoms; $R_{14}$ is a hydrogen atom, a lower alkyl radical, an alkenyl radical, an alkynyl radical, a $C_3$–$C_6$ cycloaliphatic radical, a mono- or polyhydroxyalkyl radical, said hydroxyls optionally being protected as methoxy, acetoxy or acetonide groups, an aryl or aralkyl radical, a —CO—$R_8$ radical, a —COO$R_9$ radical, an —S(O)$_p$—$R_{10}$ radical, a radical:

or, but only in the event that n is equal to 0 and $R_3$ is —(Y)$_n$—$(CH_2)$$R_{14}$, a hydroxyl radical, an —O—$R_{12}$ radical or an —O—CO$R_{12}$ radical; and Y is an oxygen or sulfur atom or an —S(O)$_p$ radical; or a pharmaceutically/cosmetically acceptable salt or optical or geometric isomer thereof.

2. An adamantyl-substituted polycyclic acetylene compound as defined by claim 1, wherein formula (I), Ar has the structure (a).

3. An adamantyl-substituted polycyclic acetylene compound as defined by claim 1, wherein formula (I), Ar has the structure (b).

4. An adamantyl-substituted polycyclic acetylene compound as defined by claim 1, wherein formula (I), Ar has the structure (c).

5. An adamantyl-substituted polycyclic acetylene compound as defined by claim 1, wherein formula (I), Ar has the structure (d).

6. An adamantyl-substituted polycyclic acetylene compound as defined by claim 1, wherein formula (I), Ar has the structure (e).

7. An adamantyl-substituted polycyclic acetylene compound as defined by claim 1, wherein formula (I), Ar has the structure (f).

8. An adamantyl-substituted polycyclic acetylene compound as defined by claim 1, comprising a pharmaceutically acceptable salt thereof.

9. An adamantyl-substituted polycyclic acetylene compound as defined by claim 1, wherein formula (I), the lower alkyl radical substituents are selected from among methyl, ethyl, isopropyl, butyl, tert-butyl and hexyl radicals.

10. An adamantyl-substituted polycyclic acetylene compound as defined by claim 1, wherein formula (I), the linear or branched alkyl radical substituents having from 1 to 20 carbon atoms are selected from among methyl, ethyl, propyl, 2-ethylhexyl, octyl, dodecyl, hexadecyl and octadecyl radicals.

11. An adamantyl-substituted polycyclic acetylene compound as defined by claim 1, wherein formula (I), the monohydroxyalkyl radical substituents are selected from among 2-hydroxypropyl and 3-hydroxypropyl radicals.

12. An adamantyl-substituted polycyclic acetylene compound as defined by claim 1, wherein formula (I), the polyhydroxyalkyl radical substituents are selected from among 2,3-dihydroxypropyl, 2,3,4-trihydroxybutyl, 2,3,4,5-tetrahydroxypentyl and pentaerythritol radicals.

13. An adamantyl-substituted polycyclic acetylene compound as defined by claim 1, wherein formula (I), the aryl radical substituents are selected from among phenyl radicals optionally substituted by at least one halogen atom, or a hydroxyl or nitro functional group.

14. An adamantyl-substituted polycyclic acetylene compound as defined by claim 1, wherein formula (I), the aralkyl radical substituents are selected from among benzyl and phenethyl radicals optionally substituted by at least one halogen atom, or a hydroxyl or nitro functional group.

15. An adamantyl-substituted polycyclic acetylene compound as defined by claim 1, wherein formula (I), the alkenyl radical substituents have from 2 to 5 carbon atoms and comprise at least one site of ethylenic unsaturation.

16. An adamantyl-substituted polycyclic acetylene compound as defined by claim 1, wherein formula (I), the alkynyl radical substituents have from 2 to 6 carbon atoms.

17. An adamantyl-substituted polycyclic acetylene compound as defined by claim 1, wherein formula (I), the sugar residue substituents are selected from among those of glucose, galactose, mannose and glucuronic acid.

18. An adamantyl-substituted polycyclic acetylene compound as defined by claim 1, wherein formula (I), the amino acid residue substituents are selected from among those of lysine, glycine and aspartic acid.

19. An adamantyl-substituted polycyclic acetylene compound as defined by claim 1, wherein formula (I), the peptide residue substituents are those of a dipeptide or tripeptide.

20. An adamantyl-substituted polycyclic acetylene compound as defined by claim 1, wherein formula (I), the heterocyclic radical substituents are selected from among piperidino, morpholino, pyrrolidino and piperazino radicals which are optionally substituted by a $C_1$–$C_6$ alkyl radical or a mono- or polyhydroxyalkyl radical.

21. An adamantyl-substituted polycyclic acetylene compound as defined by claim 1, wherein formula (I), the halogen atom substituents are selected from among fluorine, chlorine and bromine atoms.

22. An adamantyl-substituted polycyclic acetylene compound as defined by claim 1, selected from among 4-[3-(1-adamantyl)-4-methoxyphenylethynyl]benzoic acid; 4-[3-(1-adamantyl)-4-methoxyethoxymethoxyphenylethynyl] benzoic acid; 4-[3-(1-adamantyl)-4-hydroxyphenylethynyl] benzoic acid; 5-[3-(1-adamantyl)-4-methoxyphenylethynyl] -2-thiophenecarboxylic acid; 5-[3-(1-adamantyl)-4-hydroxyphenylethynyl]-2-thiophenecarboxylic acid; 2-[3-(1-adamantyl)-4-methoxyphenylethynyl]-4-thiophenecarboxylic acid; 6-[3-(1-adamantyl)-4-methoxyphenylethynyl]-2-naphthoic acid; 4-[3-(1-adamantyl)-4-nonyloxyphenylethynyl]benzoic acid; 4-[3-(1-adamantyl)-4-hexyloxyphenylethynyl]benzoic acid; 4-[3-(1-adamantyl)-4-dodecyloxyphenyl-ethynyl]benzoic acid; 4-[3-(1-adamantyl)-4-cyclopropylmethoxyphenyl-ethynyl]benzoic acid; 4-[2-hexyloxy-5-(1-adamantyl)-4-hexyloxyphenyl-ethynyl]benzoic acid; 4-[3-(1-adamantyl)-4-heptyloxyphenylethynyl]benzoic acid; 6-[3-(1-adamantyl)-4-methoxyethoxymethoxyphenylethynyl]nicotinic acid; 4-[2-methoxy-5-(1-adamantyl)-4-methoxyphenyl-ethynyl] benzoic acid; 4-[2-methoxyethoxymethoxy-5-(1-adamantyl)-4-methoxyethoxymethoxyphenylethynyl]benzoic acid; 4-[2-methoxy-5-(1-adamantyl)-4-methoxyethoxymethoxyphenylethynyl]benzoic acid; 4-[3-(1-adamantyl)-4-benzyloxyphenylethynyl]benzoic acid; 4-[3-(1-adamantyl)-4-methoxyethoxymethoxyphenyl-ethynyl]benzaldehyde; 4-[3-(1-adamantyl)-4-methoxyethoxymethoxyphenyl-ethynyl]benzenemethanol; 4-[3-(1-adamantyl)-4-methoxyethoxymethoxyphenyl-ethynyl]benzyl acetate; 4-[3-(1-adamantyl)-4-methoxyethoxymethoxyphenylethynyl]phenyl acetate; 4-[3-(1-adamantyl)-4-methoxyethoxymethoxyphenyl-ethynyl]phenol; 4-[3-(1-adamantyl)-4-methoxyethoxymethoxyphenylethynyl]phenoxyethylmorpholine; 4-[3-(1-adamantyl)-4-methoxyethoxymethoxyphenyl-ethynyl]benzamide; N-ethyl-4 -[3-(1-adamantyl)-4-methoxyethoxymethoxyphenylethynyl]benzamide; 4-[3-(1-adamantyl)-4-methoxyethoxymethoxyphenyl-ethynyl]benzoic acid morpholide; 2-hydroxy-4-[3-(1-adamantyl)-4-methoxyethoxy-methoxyphenylethynyl]benzoic acid; 4-[3-(1-adamantyl)-4-(6-hydroxyhexyloxy)phenylethynyl]benzoic acid; 4-[3-(1-adamantyl)-4-(6-methoxyhexyloxy)phenylethynyl]benzoic acid; 4-[[3-(1-adamantyl)-4-[2-(4-morpholino)ethoxy]phenylethynyl]]benzoic acid; 4-[3-(1-adamantyl)-4-(3-carbamoylpropyloxy)phenyl-ethynyl]benzoic acid; 4-[3-(1-adamantyl)-4-(5-carbamoylpentyloxy)phenylethynyl]benzoic acid; 4-[3-(1-adamantyl)-4-(3-hydroxypropyloxy)phenylethynyl]benzoic acid; 4-[3-(1-adamantyl)-4-(3-hydroxy-2-methylpropyloxy)-phenylethynyl]benzoic acid; 4-[3-(1-adamantyl)-4-[(2,2-dimethyl1,3-dioxolan-4-methoxy)phenylethynyl]benzoic acid; 4-[3-(1-adamantyl)-4-(2,3-dihydroxypropyloxy)-phenylethynyl]benzoic acid; 4-[3-(1-adamantyl)-4-methoxyethoxyethylphenylethynyl] benzoic acid; 4-[3-(1-adamantyl)-4-methoxymethoxy-propylphenyl-ethynyl]benzoic acid; 4-[3-(1-adamantyl)-4-methoxyethoxypropylphenyl-ethynyl]benzoic acid; 4-[3-(1-adamantyl)-4-acetoxybutoxyphenyl-ethynyl]benzoic acid; and 4-[3-(1-adamantyl)-4-acetoxypropyloxyphenylethynyl] benzoic acid.

23. An adamantyl-substituted polycyclic acetylene compound as defined by claim 8, comprising an alkali or alkaline earth metal, zinc or amine salt.

24. An adamantyl-substituted polycyclic acetylene compound as defined by claim 1, wherein formula (I), at least one of the following definitions exist:

$R_1$ is a —$(CH_2)_p$—CO—$R_8$ radical;

$R_3$ is an —O—$CH_2$—O—$CH_2$—$CH_2$—O—$CH_3$ or —(Y—)$_n$—(CH$_2$—)$_q$—$R_{14}$ radical;

Ar is a radical selected from among those of formulae (a) and (e); and $R_2$ is a linear or branched alkyl radical having from 1 to 20 carbon atoms or an —O—$R_{13}$ radical.

25. A pharmaceutical composition of matter, comprising a therapeutically effective amount of an adamantyl-substituted polycyclic acetylene compound as defined by claim 1, or pharmaceutically acceptable salt or isomer thereof, and a pharmaceutically acceptable vehicle, carrier or diluent therefor.

26. The pharmaceutical composition as defined by claim 25, further comprising a retinoid compound, a D vitamin or derivative thereof, a corticosteroid, an anti-free radical agent, an α-hydroxy or α-keto acid or derivative thereof, an ion channel blocker, or combination thereof.

27. The pharmaceutical composition as defined by claim 25, comprising a tablet, a capsule, a syrup, a dragee, a suspension, an elixir, a solution, a powder, granules, an emulsion, microspheres, nanospheres, lipid vesicles, polymeric vesicles, or an injectable.

28. The pharmaceutical composition as defined by claim 25, comprising an ointment, a cream, a milk, a salve, an impregnated pad, a gel, a spray, or a lotion.

29. The pharmaceutical composition as defined by claim 25, adopted for topical administration.

30. The pharmaceutical composition as defined by claim 25, adopted for systemic administration.

31. The pharmaceutical composition as defined by claim 25, comprising from 0.001% to 5% by weight of said adamantyl-substituted polycyclic acetylene compound, or salt or isomer thereof.

32. A method for treating a dermatological, rheumatic, respiratory, cardiovascular, bone or ophthalmologic disorder in a mammalian organism in need of such treatment, comprising administering to such organism a therapeutically effective amount of the pharmaceutical composition as defined by claim 25.

33. A method for treating osteoporosis in a mammalian organism in need of such treatment, comprising administering to such organism a therapeutically effective amount of the pharmaceutical composition as defined by claim 25.

34. The method as defined by claim 32, comprising administering to such organism a daily dose of said adamantyl-substituted polycyclic acetylene compound of about 0.01 mg/kg to 100 mg/kg of body weight thereof.

35. A cosmetic composition of matter, comprising a cosmetically effective amount of an adamantyl-substituted polycyclic acetylene compound as defined by claim 1, or cosmetically acceptable salt or isomer thereof, and a cosmetically acceptable vehicle, carrier or diluent therefor.

36. The cosmetic composition as defined by claim 35, comprising a cream, a milk, a lotion, a gel, an ointment, microspheres, nanospheres, lipid vesicles, polymeric vesicles, a soap, or a shampoo.

37. The cosmetic composition as defined by claim 35, comprising from 0.001% to 3% by weight of said adamantyl-substituted polycyclic acetylene compound, or salt or isomer thereof.

38. The cosmetic composition as defined by claim 35, further comprising a retinoid compound, a D vitamin or derivative thereof, a corticosteroid, an anti-free radical agent, an α-hydroxy or α-keto acid or derivative thereof, an ion channel blocker, or combination thereof.

39. The pharmaceutical composition as defined by claim 25, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

40. The pharmaceutical composition as defined by claim 25, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

41. The cosmetic composition by claim 35, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

42. The cosmetic composition as defined by claim 35, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

\* \* \* \* \*